(12) United States Patent
Nakagaki et al.

(10) Patent No.: US 11,378,543 B2
(45) Date of Patent: Jul. 5, 2022

(54) GAS SENSOR AND SENSOR ELEMENT

(71) Applicant: NGK INSULATORS, LTD., Aichi (JP)

(72) Inventors: Kunihiko Nakagaki, Nagoya (JP); Taku Okamoto, Nagoya (JP); Osamu Nakasone, Inabe (JP); Nobukazu Ikoma, Nagoya (JP)

(73) Assignee: NGK INSULATORS, LTD., Nagoya (JP)

(*) Notice: Subject to any disclaimer, the term of this patent is extended or adjusted under 35 U.S.C. 154(b) by 208 days.

(21) Appl. No.: 16/452,584

(22) Filed: Jun. 26, 2019

(65) Prior Publication Data

US 2020/0003725 A1 Jan. 2, 2020

(30) Foreign Application Priority Data

Jul. 2, 2018 (JP) .............................. JP2018-126301
Mar. 27, 2019 (JP) .............................. JP2019-059955

(51) Int. Cl.
*G01N 27/419* (2006.01)
*G01N 27/407* (2006.01)
(Continued)

(52) U.S. Cl.
CPC ....... *G01N 27/4075* (2013.01); *F01N 11/007* (2013.01); *G01N 27/409* (2013.01);
(Continued)

(58) Field of Classification Search
CPC .. G01N 27/409; G01N 27/41; G01N 27/4075; G01N 27/4071; G01N 33/0037; G01N 33/0054
See application file for complete search history.

(56) References Cited

U.S. PATENT DOCUMENTS 5,603,216 A * 2/1997 Guile .................... F01N 3/0835
60/288
6,401,522 B1 6/2002 Kon et al.
(Continued)

FOREIGN PATENT DOCUMENTS

| JP | 2011-039041 A | 2/2011 |
| JP | 2014-190940 A | 10/2014 |
| JP | 6447568 B2 | 1/2019 |

OTHER PUBLICATIONS

Unexamined U.S. Appl. No. 16/452,593, filed Jun. 26, 2019.
U.S. Appl. No. 16/819,813 filed Mar. 16, 2020.

*Primary Examiner* — Alexander S Noguerola
(74) *Attorney, Agent, or Firm* — Mattingly & Malur, PC

(57) ABSTRACT

A gas sensor includes an element body, an inner main pump electrode, an inner auxiliary pump electrode, an inner preliminary pump electrode, a measurement electrode, a reference electrode, a measurement voltage detection device, a specific gas concentration detection device. The inner preliminary pump electrode, the inner main pump electrode, the inner auxiliary pump electrode and the measurement electrode include each contain a noble metal having catalytic activity. At least one of the inner preliminary pump electrode and the inner main pump electrode contains no noble metal having a catalytic activity suppression ability, the catalytic activity suppression ability being an ability to suppress the catalytic activity of the noble metal having the catalytic activity from being exhibited to the specific gas. The inner auxiliary pump electrode contains a noble metal having the catalytic activity suppression ability.

10 Claims, 4 Drawing Sheets

(51) Int. Cl.
*F01N 11/00* (2006.01)
*G01N 33/00* (2006.01)
*G01N 27/409* (2006.01)

(52) U.S. Cl.
CPC ..... *G01N 27/4074* (2013.01); *G01N 27/4077* (2013.01); *G01N 27/419* (2013.01); *G01N 33/0037* (2013.01); *F01N 2550/02* (2013.01)

(56) References Cited

U.S. PATENT DOCUMENTS

| | | | | |
|---|---|---|---|---|
| 7,062,904 | B1* | 6/2006 | Hu | F01N 3/0842 60/297 |
| 2001/0000598 | A1* | 5/2001 | Miyata | G01N 27/419 204/426 |
| 2001/0023823 | A1* | 9/2001 | Takahashi | G01N 33/0037 204/426 |
| 2003/0106795 | A1* | 6/2003 | Katafuchi | G01N 27/4071 204/427 |
| 2011/0011152 | A1 | 1/2011 | Ito et al. | |
| 2016/0258897 | A1* | 9/2016 | Sakakibara | G01N 27/419 |
| 2017/0315019 | A1 | 11/2017 | Serizawa et al. | |

* cited by examiner

GAS SENSOR AND SENSOR ELEMENT

CROSS-REFERENCE TO RELATED APPLICATION

The present application claims priority from Japanese Patent Application No. 2019-059955 filed on Mar. 27, 2019 and Japanese Patent Application No. 2018-126301 filed on Jul. 2, 2018, the entire contents of which are incorporated herein by reference.

BACKGROUND OF THE INVENTION

1. Field of the Invention

The present invention relates to a gas sensor and a sensor element.

2. Description of the Related Art

In the related art, a gas sensor is known for detecting the specific gas concentration, such as NOx, present in a measurement-object gas, such as automobile exhaust gases. For example, Patent Literature 1 describes a gas sensor including a layered body that includes a plurality of oxygen-ion-conductive solid electrolyte layers and electrodes provided on the solid electrolyte layers. When the concentration of NOx is to be detected by using this gas sensor, first, oxygen is pumped to the inside or outside by a measurement-object gas flow section, which is within the sensor element, and a portion outside of the sensor element, thereby adjusting the oxygen concentration of the measurement-object gas flow section. Subsequently, NOx in the measurement-object gas, which is a gas after the oxygen concentration is adjusted, is reduced, and the concentration of NOx in the measurement-object gas is detected based on a current that flows at an electrode (measurement electrode) within the sensor element in accordance with the oxygen concentration after the reduction. Furthermore, Patent Literature 2 describes a gas sensor for detecting the concentration of ammonia present in a measurement-object gas. The gas sensor detects the concentration of ammonia as follows. Ammonia is converted to NOx by being oxidized with oxygen present in the measurement-object gas, and the concentration of NOx derived from the ammonia is detected by using a method similar to that of Patent Literature 1.

Furthermore, Patent Literature 1 describes the following. An inner pump electrode of a pump cell for adjusting the oxygen concentration is located in the measurement-object gas flow section, and the inner pump electrode is a cermet electrode containing Pt and $ZrO_2$ and containing 1% Au. Since the inner pump electrode contains Au, the inner pump electrode is prevented from reducing NOx. On the other hand, Patent Literature 3 describes the following. In association with the use of a gas sensor, Au evaporates from an electrode of a pump cell and adheres to an electrode of a sensor cell for detecting the concentration of NOx present in a measurement-object gas. As a result, a NOx concentration detection accuracy decreases.

CITATION LIST

Patent Literature

PTL 1: Japanese Unexamined Patent Application Publication No. 2014-190940

PTL 2: Japanese Unexamined Patent Application Publication No. 2011-039041

PTL 3: Japanese Patent No. 6447568

SUMMARY OF THE INVENTION

As described above, it was necessary to include Au in the inner pump electrode because, if the inner pump electrode reduces NOx, a NOx concentration detection accuracy decreases. On the other hand, as described above, there was a problem in that, as a result of the presence of Au in the inner pump electrode, a NOx concentration detection accuracy decreases in association with the use of the gas sensor.

The present invention has been made to solve such problems, and a principal object of the present invention is to maintain a specific gas concentration detection accuracy over a long period of time.

To solve the problems described above, the present inventors diligently performed studies and consequently found that, when a vicinity of the inner pump electrode is not a low-oxygen atmosphere, substantially no reduction of NOx attributable to the inner pump electrode occurs even in a case where the inner pump electrode contains no Au. Further, it was found that the need for inclusion of Au in the inner pump electrode, which has been believed to be essential in the related art, can be eliminated by ensuring that oxygen is pumped into the measurement-object gas flow section. Accordingly, the present invention was made.

A gas sensor of the present invention includes an element body, a main pump cell, an auxiliary pump cell, a preliminary pump cell, a measurement electrode, a reference electrode, a measurement voltage detection device, and a specific gas concentration detection device. The element body includes an oxygen-ion-conductive solid electrolyte layer, and a measurement-object gas flow section is provided within the element body to allow a measurement-object gas to be introduced into the measurement-object gas flow section and flow through the measurement-object gas flow section. The main pump cell pumps oxygen from a first internal space to adjust an oxygen concentration of the first internal space, the first internal space being provided in the measurement-object gas flow section. The auxiliary pump cell pumps oxygen from a second internal space to adjust an oxygen concentration of the second internal space, the second internal space being provided downstream of the first internal space in the measurement-object gas flow section. The preliminary pump cell pumps oxygen into a preliminary chamber to prevent the measurement-object gas from reaching the first internal space in a state in which the measurement-object gas is a low-oxygen atmosphere, the preliminary chamber being provided upstream of the first internal space in the measurement-object gas flow section. The measurement electrode is disposed on an inner peripheral surface of a measurement chamber, the measurement chamber being provided downstream of the second internal space in the measurement-object gas flow section. The reference electrode is disposed within the element body. A reference gas is to be introduced to the reference electrode. The reference gas serves as a reference for detecting a specific gas concentration in the measurement-object gas. The measurement voltage detection device detects a measurement voltage present between the reference electrode and the measurement electrode. The specific gas concentration detection device obtains, based on the measurement voltage, a detection value according to produced in the measurement chamber and, based on the detection value, detects the specific gas concentration in the measurement-object gas, the oxygen being oxygen derived from the specific gas. The preliminary pump cell includes an inner preliminary pump electrode disposed in the preliminary chamber. The main pump cell includes an inner main pump electrode disposed in the first internal space. The auxiliary pump cell includes an inner auxiliary pump electrode disposed in the second internal space. The inner preliminary pump electrode, the inner main pump electrode, the inner auxiliary pump electrode, and the measurement electrode each contain a noble metal having catalytic activity. At least one of the inner preliminary pump electrode and the inner main pump electrode contains no noble metal having a catalytic activity suppression ability. The catalytic activity suppression ability is an ability to suppress the catalytic activity of the noble metal having the catalytic activity from being exhibited to the specific gas. The inner auxiliary pump electrode contains a noble metal having the catalytic activity suppression ability.

In the gas sensor, the preliminary pump cell pumps oxygen into the preliminary chamber provided upstream of the first internal space. This is to prevent the measurement-object gas from reaching the first internal space in a state in which the measurement-object gas is a low-oxygen atmosphere. Next, the main pump cell and the auxiliary pump cell individually pump oxygen from the measurement-object gas, which contains oxygen pumped into the preliminary chamber as described above. Thus, the oxygen concentration of the measurement-object gas is adjusted. As a result, after the oxygen concentration is adjusted, the measurement-object gas reaches the measurement chamber. Further, the gas sensor obtains, based on the measurement voltage, a detection value according to produced in the measurement chamber, the oxygen being oxygen derived from the specific gas, and based on the obtained detection value, the gas sensor detects the specific gas concentration in the measurement-object gas. It is to be noted that, in the gas sensor of the present invention, as described above, the preliminary pump cell supplies oxygen to the measurement-object gas prior to adjustment of the oxygen concentration. Thus, even in a case where the measurement-object gas is a low-oxygen atmosphere before being introduced into the measurement-object gas flow section, vicinities of the inner preliminary pump electrode and the inner main pump electrode are prevented from becoming a low-oxygen atmosphere. As a result, even in a case where at least one of the inner preliminary pump electrode and the inner main pump electrode contains no noble metal (e.g., Au) having a catalytic activity suppression ability, neither reduction of a specific gas due to the electrode nor reduction of an oxide derived from the specific gas due to the electrode is likely to occur. Hence, a sufficient specific gas detection accuracy is achieved. Furthermore, since at least one of the inner preliminary pump electrode and the inner main pump electrode contains no noble metal having a catalytic activity suppression ability, an instance in which noble metal evaporates and adheres to the measurement electrode, which may otherwise occur in association with the use of the gas sensor, is suppressed from occurring. Accordingly, the gas sensor of the present invention has a specific gas concentration detection accuracy that is maintained over a long period of time.

It is to be noted that the phrase "measurement-object gas that is a low-oxygen atmosphere" encompasses cases in which the measurement-object gas is a rich-atmosphere gas containing unburned fuel. Furthermore, the phrase "contains no noble metal having a catalytic activity suppression ability" means that substantially no noble metal having a catalytic activity suppression ability is included, and it is therefore possible that one or more noble metals having a catalytic activity suppression ability are included as incidental impurities. The first internal space may be referred to as "oxygen concentration adjustment chamber". The main pump cell may be referred to as "adjustment pump cell".

It is to be noted that, in the case where the specific gas is an oxide, the phrase "oxygen produced in the measurement chamber, the oxygen being oxygen derived from the specific gas" may refer to oxygen produced when the specific gas itself is reduced in the measurement chamber. In the case where the specific gas is a non-oxide gas, the phrase "oxygen produced in the measurement chamber, the oxygen being oxygen derived from the specific gas" may refer to oxygen produced when the specific gas is converted into an oxide and the resulting gas is reduced in the measurement chamber. Furthermore, the specific gas concentration detection device may obtain the detection value as follows. Based on the measurement voltage, oxygen produced in the measurement chamber may be pumped from the measurement chamber to the outside, the oxygen being oxygen derived from the specific gas, so that the oxygen concentration in the measurement chamber can reach a predetermined low concentration. When the pumping is performed, a measurement pump current flows. The measurement pump current may be the detection value. The element body may be a layered body including a plurality of stacked oxygen-ion-conductive solid electrolyte layers.

The gas sensor of the present invention may further include a preliminary pump control device. The preliminary pump control device may control the preliminary pump cell in a manner such that a constant preliminary pump current flows through the preliminary pump cell. With this configuration, oxygen can be supplied, by performing a relatively simple control, to a measurement-object gas that is a low-oxygen atmosphere in the preliminary chamber.

The gas sensor of the present invention may further include a storage device. The storage device may store information related to a relationship formula representing a relationship between the detection value and the specific gas concentration. Regardless of whether a measurement-object gas that is outside of the element body is a low-oxygen atmosphere, the specific gas concentration detection device may detect the specific gas concentration by using the same relationship formula stored in the storage device. In this manner, the gas sensor of the present invention can detect the specific gas concentration accurately without using different relationship formulas for the case in which the measurement-object gas is a low-oxygen atmosphere and for the case in which the measurement-object gas is not a low-oxygen atmosphere. Hence, the gas sensor can detect the specific gas concentration readily and accurately.

In the gas sensor of the present invention, the specific gas concentration detection device detects the specific gas concentration, and the specific gas concentration may be a concentration corrected based on an oxygen concentration of the measurement-object gas that is outside of the element body. It is to be noted that, even in the case where the actual concentration (real concentration) of a specific gas in a measurement-object gas is uniform, the detection value may change with the oxygen concentration of a measurement-object gas that is outside of the element body, and in this case, the specific gas concentration measured based on the detection value also changes. Accordingly, by detecting the specific gas concentration by involving the oxygen-concentration-based correction, a specific gas concentration measurement accuracy is improved. The phrase "detect the specific gas concentration, and the specific gas concentration is a concentration corrected based on an oxygen concentration of the measurement-object gas" encompasses the following: cases in which the specific gas concentration is detected based on a detection value obtained after the oxygen-concentration-based correction; and cases in which, when detecting the specific gas concentration based on the detection value, the oxygen-concentration-based correction is performed, and the corrected the specific gas concentration is detected.

In this case, the gas sensor of the present invention may further include a preliminary pump control device and an oxygen concentration detection device. The preliminary pump control device may control the preliminary pump cell in a manner such that a constant preliminary pump current flows through the preliminary pump cell. The oxygen concentration detection device may detect the oxygen concentration of the measurement-object gas that is outside of the element body. The oxygen concentration may be detected based on the constant preliminary pump current, a pump current that flows when the main pump cell pumps oxygen from the first internal space in a manner such that the oxygen concentration of the first internal space reaches a target concentration, and the target concentration. The specific gas concentration detection device may correct the specific gas concentration by using the oxygen concentration detected by the oxygen concentration detection device. It is to be noted that the constant preliminary pump current that flows through the preliminary pump cell corresponds to the flow rate of oxygen pumped into the measurement-object gas flow section by the preliminary pump cell. Furthermore, the pump current of the main pump cell corresponds to the flow rate of oxygen pumped from the first internal space. Hence, the oxygen concentration of a measurement-object gas outside of the element body can be detected based on the currents and the target concentration. That is, the oxygen concentration necessary for correction can be detected by the gas sensor of the present invention.

The gas sensor of the present invention may further include a measurement-object gas-side electrode disposed at a portion that is to be exposed to the measurement-object gas that is outside of the element body. The preliminary pump cell may pump oxygen into the preliminary chamber from a vicinity of the measurement-object gas-side electrode. With this configuration, the following is possible. In comparison with, for example, a case in which oxygen is pumped into the preliminary chamber from a vicinity of the reference electrode, a decrease in measurement accuracy that may occur when the potential of the reference electrode changes as a result of a voltage drop due to the current during pumping is suppressed.

In the gas sensor of the present invention, the measurement-object gas may be an exhaust gas from an internal combustion engine, the reference gas may be air, and the preliminary pump cell may pump oxygen into the preliminary chamber from a vicinity of the reference electrode. With this configuration, the following is possible. In comparison with, for example, a case in which oxygen is pumped to the inside from exhaust gases that are outside of the element body, oxygen can be pumped into the preliminary chamber at a low applied voltage because air has a higher oxygen concentration than exhaust gases.

In the gas sensor of the present invention, neither the inner preliminary pump electrode nor the inner main pump electrode may contain a noble metal having the catalytic activity suppression ability. With this configuration, the effect of maintaining a specific gas concentration detection accuracy over a long period of time is enhanced.

In the gas sensor of the present invention, the inner auxiliary pump electrode contains the noble metal having the catalytic activity suppression ability, and the noble metal may include Au.

A sensor element of the present invention includes an element body, a main pump cell, an auxiliary pump cell, a preliminary pump cell, a measurement electrode, a reference electrode, a measurement voltage detection device, and a specific gas concentration detection device. The element body includes an oxygen-ion-conductive solid electrolyte layer, and a measurement-object gas flow section is provided within the element body to allow a measurement-object gas to be introduced into the measurement-object gas flow section and flow through the measurement-object gas flow section. The main pump cell pumps oxygen from a first internal space to adjust an oxygen concentration of the first internal space, the first internal space being provided in the measurement-object gas flow section. The auxiliary pump cell pumps oxygen from a second internal space to adjust an oxygen concentration of the second internal space, the second internal space being provided downstream of the first internal space in the measurement-object gas flow section. The preliminary pump cell pumps oxygen into a preliminary chamber provided upstream of the first internal space in the measurement-object gas flow section. The measurement electrode is disposed on an inner peripheral surface of a measurement chamber, the measurement chamber being provided downstream of the second internal space in the measurement-object gas flow section. The reference electrode is disposed within the element body. A reference gas is to be introduced to the reference electrode. The reference gas serves as a reference for detecting a specific gas concentration in the measurement-object gas. The preliminary pump cell includes an inner preliminary pump electrode disposed in the preliminary chamber. The main pump cell includes an inner main pump electrode disposed in the first internal space. The auxiliary pump cell includes an inner auxiliary pump electrode disposed in the second internal space. The inner preliminary pump electrode, the inner main pump electrode, the inner auxiliary pump electrode, and the measurement electrode each contain a noble metal having catalytic activity. At least one of the inner preliminary pump electrode and the inner main pump electrode contains no noble metal having a catalytic activity suppression ability. The catalytic activity suppression ability is an ability to suppress the catalytic activity of the noble metal having the catalytic activity from being exhibited to the specific gas. The inner auxiliary pump electrode contains a noble metal having the catalytic activity suppression ability.

By using the sensor element, the specific gas concentration in a measurement-object gas can be detected, as with the above-described gas sensor of the present invention. Furthermore, in the sensor element, as with the above-described gas sensor of the present invention, at least one of the inner preliminary pump electrode and the inner main pump electrode contains no noble metal having a catalytic activity suppression ability, and the inner auxiliary pump electrode contains a noble metal having a catalytic activity suppression ability. Consequently, in the case where the sensor element is used to detect the specific gas concentration in a measurement-object gas, a specific gas concentration detection accuracy can be maintained over a long period of time.

DETAILED DESCRIPTION OF THE INVENTION

Figure 1:
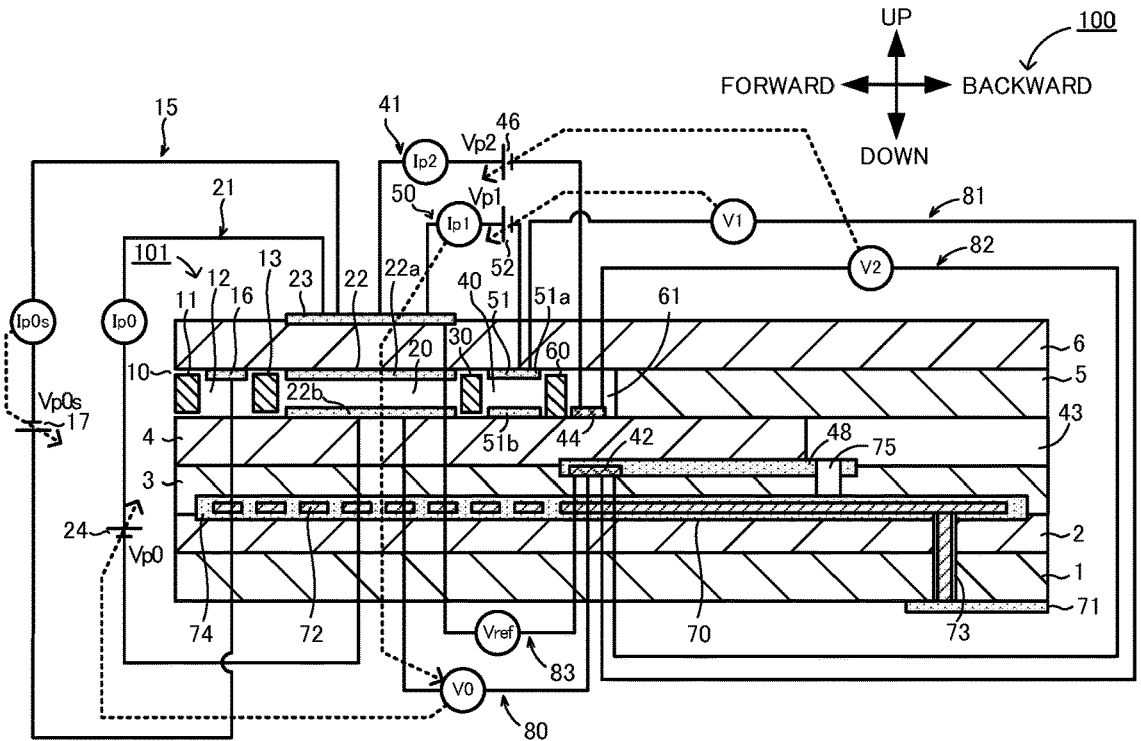
FIG. 1 is a schematic cross-sectional view of a gas sensor 100.
Figure 2:
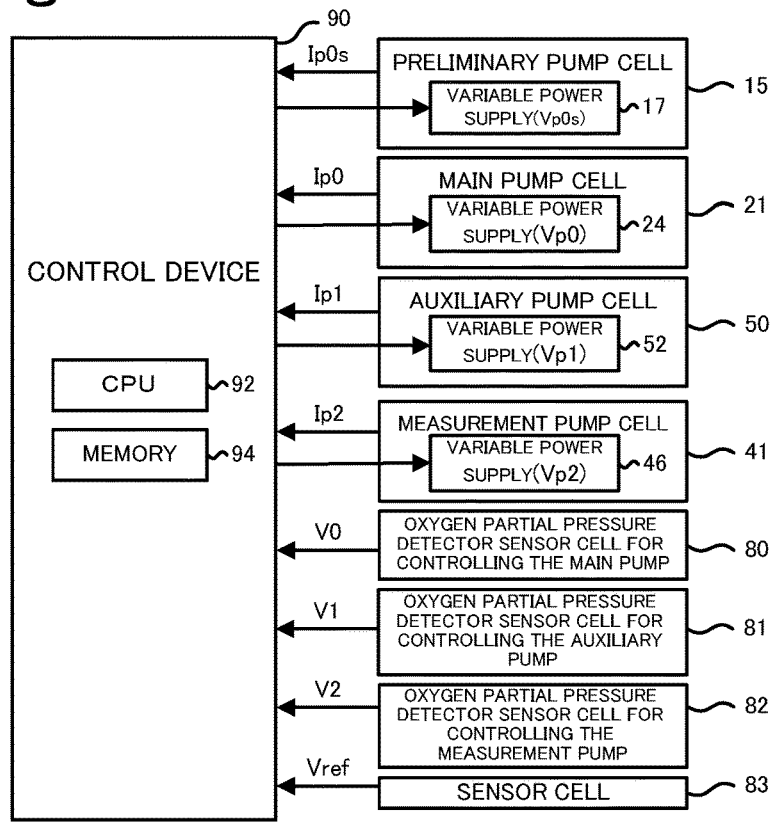
FIG. 2 is a block diagram illustrating an electrical connection relationship between a controller 90 and individual cells.

An embodiment of the present invention will now be described with reference to the drawings. FIG. 1 is a schematic cross-sectional view schematically illustrating an example of a configuration of a gas sensor 100, which is an embodiment of the present invention. FIG. 2 is a block diagram illustrating an electrical connection relationship between a controller 90 and individual cells. The gas sensor 100 is attached to, for example, a pipe such as an exhaust gas pipe of an internal combustion engine, examples of which include gasoline engines and diesel engines. The gas sensor 100 detects the specific gas concentration in a measurement-object gas, which is exhaust gases from an internal combustion engine. Examples of the specific gas include NOx and ammonia. In the present embodiment, the specific gas concentration measured by the gas sensor 100 is the concentration of NOx. The gas sensor 100 includes a sensor element 101, cells 15, 21, 41, 50, and 80 to 83, and a controller 90. The sensor element 101 has an elongated parallelepiped shape. Each of the cells 15, 21, 41, 50, and 80 to 83 includes a portion of the sensor element 101. The controller 90 controls the gas sensor 100 as a whole.

The sensor element 101 is an element including a layered body in which six layers, namely a first substrate layer 1, a second substrate layer 2, a third substrate layer 3, a first solid electrolyte layer 4, a spacer layer 5, and a second solid electrolyte layer 6, are layered in this order from the bottom side, as viewed in the drawing. Each of the six layers is formed of an oxygen-ion-conductive solid electrolyte layer containing, for example, zirconia ($ZrO_2$). Furthermore, the solid electrolyte forming each of the six layers is dense and gas-tight. The sensor element 101 is produced as follows, for example. Ceramic green sheets corresponding to the respective layers are subjected to, for example, a predetermined process and circuit pattern printing. The resulting sheets are then layered together and subjected to firing to be unified.

On the front side (left side of FIG. 1) of the sensor element 101, a gas inlet port 10, a first diffusion-rate-limiting portion 11, a buffer space 12, a second diffusion-rate-limiting portion 13, a first internal space 20, a third diffusion-rate-limiting portion 30, a second internal space 40, a fourth diffusion-rate-limiting portion 60, and a third internal space 61 are formed adjacent to one another in such a manner as to be in communication with one another in this order, between the lower surface of the second solid electrolyte layer 6 and the upper surface of the first solid electrolyte layer 4.

The gas inlet port 10, the buffer space 12, the first internal space 20, the second internal space 40, and the third internal space 61 constitute a space within the sensor element 101. The space is provided in such a manner that a portion of the spacer layer 5 is hollowed out. The top of the space is defined by the lower surface of the second solid electrolyte layer 6, the bottom of the space is defined by the upper surface of the first solid electrolyte layer 4, and sides of the space are defined by side surfaces of the spacer layer 5.

The first diffusion-rate-limiting portion 11, the second diffusion-rate-limiting portion 13, and the third diffusion-rate-limiting portion 30 are each provided as two horizontally extending slits (whose openings have a longitudinal direction in a direction perpendicular to the drawing). Furthermore, the fourth diffusion-rate-limiting portion 60 is provided as one horizontally extending slit (whose opening has a longitudinal direction in a direction perpendicular to the drawing), which is formed as a gap with respect to the lower surface of the second solid electrolyte layer 6. Note that the region extending from the gas inlet port 10 to the third internal space 61 is also referred to as a "measurement-object gas flow section".

Furthermore, a reference gas introduction space 43 is provided at a position farther from the front side than is the measurement-object gas flow section. The position is between the upper surface of the third substrate layer 3 and the lower surface of the spacer layer 5, and a side of the reference gas introduction space 43 is defined by a side surface of the first solid electrolyte layer 4. A reference gas for measuring the concentration of NOx is introduced into the reference gas introduction space 43. Examples of the reference gas include air.

An air introduction layer 48 is a layer formed of a porous ceramic material. A reference gas can be introduced into the air introduction layer 48 through the reference gas introduction space 43. Furthermore, the air introduction layer 48 is formed to cover the reference electrode 42.

The reference electrode 42 is an electrode formed in such a manner as to be sandwiched between the upper surface of the third substrate layer 3 and the first solid electrolyte layer 4. As described above, the air introduction layer 48, which is coupled to the reference gas introduction space 43, is provided in a vicinity of the reference electrode 42. Furthermore, as will be described later, the reference electrode 42 can be used to measure the oxygen concentrations (oxygen partial pressures) of the first internal space 20, the second internal space 40, and the third internal space 61. The reference electrode 42 is formed as a porous cermet electrode (e.g., cermet electrode containing Pt and $ZrO_2$).

In the measurement-object gas flow section, the gas inlet port 10 is a portion open to an external space. A measurement-object gas can be drawn into the sensor element 101 through the gas inlet port 10 from an external space. The first diffusion-rate-limiting portion 11 is a portion that imparts a predetermined diffusion resistance to the measurement-object gas drawn in through the gas inlet port 10. The buffer space 12 is a space provided to guide the measurement-object gas introduced from the first diffusion-rate-limiting portion 11 to the second diffusion-rate-limiting portion 13. The buffer space 12 also serves as a space (preliminary chamber) for pumping oxygen into the measurement-object gas introduced through the first diffusion-rate-limiting portion 11. Pumping of oxygen into the buffer space 12 is carried out by the operation of a preliminary pump cell 15. The second diffusion-rate-limiting portion 13 is a portion that imparts a predetermined diffusion resistance to the measurement-object gas, which is introduced into the first internal space 20 from the buffer space 12. The measurement-object gas is introduced from outside of the sensor element 101 into the first internal space 20 as follows. Upon pressure fluctuations of a measurement-object gas in an external space (exhaust gas pressure pulsations in the case where the measurement-object gas is an automobile exhaust gas), the measurement-object gas is rapidly drawn into the sensor element 101 through the gas inlet port 10. Then, the measurement-object gas is not directly introduced into the first internal space 20 but introduced into the first internal space 20 after concentration variations of the measurement-object gas are eliminated by the first diffusion-rate-limiting portion 11, the buffer space 12, and the second diffusion-rate-limiting portion 13. As a result, concentration variations of the measurement-object gas, when being introduced into the first internal space 20, are substantially negligible. The first internal space 20 is provided as a space for adjusting the partial pressure of oxygen present in the measurement-object gas, which is introduced through the second diffusion-rate-limiting portion 13. The oxygen partial pressure is adjusted by the operation of a main pump cell 21.

The preliminary pump cell 15 is an electrochemical pump cell including a preliminary pump electrode 16, an outer pump electrode 23, and the second solid electrolyte layer 6, which is sandwiched between the electrodes. The preliminary pump electrode 16 is provided on substantially the entire surface of a portion of the lower surface of the second solid electrolyte layer 6, the portion facing the buffer space 12. The outer pump electrode 23 is disposed on a portion that is to be exposed to a measurement-object gas that is outside of the sensor element 101. Of a plurality of electrodes in the measurement-object gas flow section, the preliminary pump electrode 16 is an electrode disposed most upstream. A pump voltage Vp0s can be applied by a variable power supply 17, which is provided between the preliminary pump electrode 16 and the outer pump electrode 23, thereby passing a pump current Ip0s between the preliminary pump electrode 16 and the outer pump electrode 23. This enables the preliminary pump cell 15 to pump oxygen from an external space into the buffer space 12.

The main pump cell 21 is an electrochemical pump cell including an inner pump electrode 22, the outer pump electrode 23, and the second solid electrolyte layer 6, which is sandwiched between the electrodes. The inner pump electrode 22 includes a ceiling electrode portion 22a, which is provided on substantially the entire surface of a portion of the lower surface of the second solid electrolyte layer 6, the portion facing the first internal space 20. The outer pump electrode 23 is provided on a region of the upper surface of the second solid electrolyte layer 6, the region corresponding to the ceiling electrode portion 22a. The outer pump electrode 23 is provided in such a manner as to be exposed to an external space.

The inner pump electrode 22 is formed to extend along portions of the upper and lower solid electrolyte layers (second solid electrolyte layer 6 and first solid electrolyte layer 4), which define the first internal space 20, and along portions of the spacer layer 5, which serve as side walls. Specifically, the ceiling electrode portion 22a is formed on a portion of the lower surface of the second solid electrolyte layer 6, the portion serving as a ceiling surface of the first internal space 20; a bottom electrode portion 22b is formed on a portion of the upper surface of the first solid electrolyte layer 4, the portion serving as a bottom surface of the first internal space 20; side electrode portions (not illustrated) are formed on portions of the side wall surfaces (inner surfaces) of the spacer layer 5, the portions forming respective side wall portions of the first internal space 20, the side electrode portions connecting the ceiling electrode portion 22a to the bottom electrode portion 22b; and thus, in the region where the side electrode portions are disposed, the structure has a shape of a tunnel.

The inner pump electrode 22 and the outer pump electrode 23 are each formed as a porous cermet electrode (e.g., cermet electrode containing Pt and $ZrO_2$).

The main pump cell 21 can pump oxygen from the first internal space 20 to an external space and can pump oxygen from an external space into the first internal space 20. This can be carried out by applying a desired pump voltage Vp0 between the inner pump electrode 22 and the outer pump electrode 23, thereby passing a pump current Ip0 in the positive or negative direction between the inner pump electrode 22 and the outer pump electrode 23.

Furthermore, an electrochemical sensor cell, namely, an oxygen partial pressure detection sensor cell 80 for controlling the main pump is configured to detect the oxygen concentration (oxygen partial pressure) of the atmosphere in the first internal space 20. The electrochemical sensor cell includes the inner pump electrode 22, the second solid electrolyte layer 6, the spacer layer 5, the first solid electrolyte layer 4, the third substrate layer 3, and the reference electrode 42.

The oxygen concentration (oxygen partial pressure) in the first internal space 20 can be determined by measuring an electromotive force V0 of the oxygen partial pressure detection sensor cell 80 for controlling the main pump. In addition, the pump voltage Vp0 of a variable power supply 24 is feedback-controlled in a manner such that the electromotive force V0 becomes a constant electromotive force, thereby controlling the pump current Ip0. As a result, the oxygen concentration in the first internal space 20 can be maintained at a predetermined constant value.

The third diffusion-rate-limiting portion 30 is a portion that imparts a predetermined diffusion resistance to the measurement-object gas, which has an oxygen concentration (oxygen partial pressure) controlled in the first internal space 20 by the operation of the main pump cell 21, and guides the measurement-object gas to the second internal space 40.

The second internal space 40 is provided as a space for further adjusting, by using an auxiliary pump cell 50, the oxygen partial pressure of the measurement-object gas, which is introduced into the second internal space 40 through the third diffusion-rate-limiting portion 30 after the oxygen concentration (oxygen partial pressure) is adjusted in advance in the first internal space 20. With this configuration, the oxygen concentration in the second internal space 40 is maintained at a constant concentration precisely; hence, with the gas sensor 100, the concentration of NOx can be measured accurately.

The auxiliary pump cell 50 is an auxiliary electrochemical pump cell including an auxiliary pump electrode 51, an outer pump electrode 23, and the second solid electrolyte layer 6 (the outer pump electrode 23 here is not limited to the outer pump electrode 23 described above, and it is sufficient that the electrode be a suitable electrode positioned outside of the sensor element 101). The auxiliary pump electrode 51 includes a ceiling electrode portion 51a, which is provided on substantially the entire surface of a portion of the lower surface of the second solid electrolyte layer 6, the portion facing the second internal space 40.

The auxiliary pump electrode 51 is disposed in the second internal space 40, and the structure of the auxiliary pump electrode 51 has a shape of a tunnel similar to that of the inner pump electrode 22, which is disposed in the first internal space 20 as described above. That is, the ceiling electrode portion 51a is formed on a portion of the second solid electrolyte layer 6, the portion serving as a ceiling surface of the second internal space 40; a bottom electrode portion 51b is formed on a portion of the first solid electrolyte layer 4, the portion serving as a bottom surface of the second internal space 40; side electrode portions (not illustrated) are formed on portions of the respective wall surfaces of the spacer layer 5, the portions serving as side walls of the second internal space 40, the side electrode portions coupling the ceiling electrode portion 51a to the bottom electrode portion 51b; and thus, the structure has a shape of a tunnel.

The auxiliary pump cell 50 can pump oxygen present in the atmosphere of the second internal space 40 to an external space and can pump oxygen from an external space into the second internal space 40. This can be carried out by applying a desired voltage Vp1 between the auxiliary pump electrode 51 and the outer pump electrode 23.

Furthermore, an electrochemical sensor cell, namely, an oxygen partial pressure detection sensor cell 81 for controlling the auxiliary pump is configured to control the oxygen partial pressure of the atmosphere in the second internal space 40. The electrochemical sensor cell includes the auxiliary pump electrode 51, the reference electrode 42, the second solid electrolyte layer 6, the spacer layer 5, the first solid electrolyte layer 4, and the third substrate layer 3.

Note that the auxiliary pump cell 50 performs pumping with a variable power supply 52, the voltage of the power supply 52 being controlled based on an electromotive force V1, which is detected by the oxygen partial pressure detection sensor cell 81 for controlling the auxiliary pump. With this configuration, the partial pressure of oxygen present in the atmosphere of the second internal space 40 can be controlled to a low partial pressure that has substantially no influence on the measurement of NOx.

Furthermore, in addition to this, a pump current Ip1 is used to control the electromotive force of the oxygen partial pressure detection sensor cell 80 for controlling the main pump. Specifically, the pump current Ip1, which is a control signal, is input into the oxygen partial pressure detection sensor cell 80 for controlling the main pump, thereby controlling the electromotive force V0, and accordingly, the gradient of the partial pressure of oxygen present in the measurement-object gas, which is introduced into the second internal space 40 through the third diffusion-rate-limiting portion 30, is controlled to be consistently a constant gradient. In the case where the gas sensor is used as a NOx sensor, the oxygen concentration in the second internal space 40 is maintained at a constant value of approximately 0.001 ppm by the operation of the main pump cell 21 and the auxiliary pump cell 50.

The fourth diffusion-rate-limiting portion 60 is a portion that imparts a predetermined diffusion resistance to the measurement-object gas, which has an oxygen concentration (oxygen partial pressure) controlled in the second internal space 40 by the operation of the auxiliary pump cell 50, and guides the measurement-object gas to the third internal space 61. The fourth diffusion-rate-limiting portion 60 has a function of limiting the amount of NOx flowing into the third internal space 61.

The third internal space 61 is provided as a space for performing a process related to the measurement of the concentration of nitrogen oxide (NOx) present in the measurement-object gas, the measurement-object gas being introduced into the third internal space 61 through the fourth diffusion-rate-limiting portion 60 after the oxygen concentration (oxygen partial pressure) is adjusted in advance in the second internal space 40. The measurement of the concentration of NOx is carried out primarily by the operation of a measurement pump cell 41 in the third internal space 61.

The measurement pump cell 41 measures the concentration of NOx present in the measurement-object gas in the third internal space 61. The measurement pump cell 41 is an electrochemical pump cell including a measurement electrode 44, the outer pump electrode 23, the second solid electrolyte layer 6, the spacer layer 5, and the first solid electrolyte layer 4. The measurement electrode 44 is provided on a portion of the upper surface of the first solid electrolyte layer 4, the portion facing the third internal space 61. The measurement electrode 44 also functions as a NOx reduction catalyst that reduces NOx present in the atmosphere of the third internal space 61.

The measurement pump cell 41 can detect a pump current Ip2 by pumping out oxygen produced by decomposition of nitrogen oxide in the atmosphere of a vicinity of the measurement electrode 44 and determining the pump current Ip2 as the amount of the oxygen produced.

Furthermore, an electrochemical sensor cell, namely, an oxygen partial pressure detection sensor cell 82 for controlling the measurement pump is configured to detect the oxygen partial pressure of a vicinity of the measurement electrode 44. The electrochemical sensor cell includes the first solid electrolyte layer 4, the third substrate layer 3, the measurement electrode 44, and the reference electrode 42. A variable power supply 46 is controlled based on an electromotive force V2, which is detected by the oxygen partial pressure detection sensor cell 82 for controlling the measurement pump.

After being guided into the second internal space 40, the measurement-object gas flows through the fourth diffusion-rate-limiting portion 60 in a situation in which the oxygen partial pressure is controlled and reaches the measurement electrode 44, which is within the third internal space 61. Nitrogen oxide in the measurement-object gas in a vicinity of the measurement electrode 44 is reduced ($2NO \rightarrow N_2 + O_2$) to produce oxygen. The produced oxygen is then pumped by the measurement pump cell 41. At that time, a voltage Vp2 of the variable power supply 46 is controlled in a manner such that the electromotive force V2, which is detected by the oxygen partial pressure detection sensor cell 82 for controlling the measurement pump, becomes a constant electromotive force. The amount of oxygen produced in a vicinity of the measurement electrode 44 is proportional to the concentration of nitrogen oxide present in the measurement-object gas. Accordingly, the concentration of nitrogen oxide present in the measurement-object gas is calculated by using the pump current Ip2 of the measurement pump cell 41.

Furthermore, an electrochemical sensor cell 83, which includes the second solid electrolyte layer 6, the spacer layer 5, the first solid electrolyte layer 4, the third substrate layer 3, the outer pump electrode 23, and the reference electrode 42, is configured. The partial pressure of oxygen present in a measurement-object gas outside of the sensor can be detected based on an electromotive force Vref, which is obtained by the sensor cell 83.

In the gas sensor 100, which is configured as described above, as a result of the operation of the main pump cell 21 and the auxiliary pump cell 50, the measurement-object gas has an oxygen partial pressure consistently maintained at a constant low value (value that has substantially no influence on the measurement of NOx), and, in this state, the measurement-object gas is provided to the measurement pump cell 41. Accordingly, the concentration of NOx present in the measurement-object gas can be determined based on the pump current Ip2, which flows when oxygen that is produced, by reduction of NOx, substantially proportionally to the concentration of NOx in the measurement-object gas, is pumped to the outside by the measurement pump cell 41.

In addition, to enhance the oxygen ion conductivity of the solid electrolyte, the sensor element 101 includes a heater unit 70, which serves to perform temperature adjustment for heating the sensor element 101 and maintaining the temperature. The heater unit 70 includes a heater connector electrode 71, a heater 72, a through hole 73, a heater insulating layer 74, and a pressure release hole 75.

The heater connector electrode 71 is an electrode formed in such a manner as to be in contact with the lower surface of the first substrate layer 1. Power can be supplied to the heater unit 70 from outside by connecting the hater connector electrode 71 to an external power source.

The heater 72 is an electrical resistor formed in such a manner as to be sandwiched by the second substrate layer 2 and the third substrate layer 3 from above and below. The heater 72 is connected to the heater connector electrode 71 via the through hole 73 and generates heat upon receiving power from outside via the heater connector electrode 71, thereby heating the solid electrolyte forming the sensor element 101 and maintaining the temperature.

Furthermore, the heater 72 is embedded over an entire area extending from the first internal space 20 to the third internal space 61 and therefore can adjust the temperature of the sensor element 101 as a whole to a temperature at which the solid electrolyte becomes active.

The heater insulating layer 74 is an insulating layer disposed adjacent to upper and lower surfaces of the heater 72 and formed of an insulating material, such as alumina. The heater insulating layer 74 is formed to provide electrical insulation between the second substrate layer 2 and the heater 72 and electrical insulation between the third substrate layer 3 and the heater 72.

The pressure release hole 75 is a portion provided to extend through the third substrate layer 3 and the air introduction layer 48 and to be in communication with the reference gas introduction space 43. The pressure release hole 75 is formed to mitigate an increase in internal pressure due to a temperature increase within the heater insulating layer 74.

The preliminary pump electrode 16, the inner pump electrode 22, the auxiliary pump electrode 51, and the measurement electrode 44 each contain a noble metal having catalytic activity. The noble metal having catalytic activity may be, for example, at least one of Pt, Rh, Ir, Ru, and Pd. The outer pump electrode 23 and the reference electrode 42 also each contain a noble metal having catalytic activity. The auxiliary pump electrode 51 also contains a noble metal having a catalytic activity suppression ability, which is an ability to suppress the catalytic activity of the above-mentioned noble metal from exhibiting to the specific gas. With this configuration, the ability of the auxiliary pump electrode 51 to reduce the NOx component present in the measurement-object gas is decreased. Examples of the noble metal having a catalytic activity suppression ability include Au. On the other hand, at least one of the preliminary pump electrode 16 and the inner pump electrode 22 contains no noble metal having a catalytic activity suppression ability. It is preferable that the measurement electrode 44 contains no noble metal having a catalytic activity suppression ability. It is also preferable that neither the outer pump electrode 23 nor the reference electrode 42 contain a noble metal having a catalytic activity suppression ability. It is preferable that each of the electrodes 16, 22, 23, 42, 44, and 51 be a cermet electrode containing a noble metal and an oxide having oxygen ion conductivity (e.g., $ZrO_2$). It is preferable that each of the electrodes 16, 22, 23, 42, 44, and 51 be a porous member. In the present embodiment, each of the electrodes 16, 22, 23, 42, and 44 is a porous cermet electrode containing Pt and $ZrO_2$. Furthermore, the auxiliary pump electrode 51 is a porous cermet electrode containing Pt and $ZrO_2$ and containing 1% Au.

The controller 90 is a microprocessor including a CPU 92, a memory 94, and the like. The controller 90 inputs the electromotive force V0, the electromotive force V1, the electromotive force V2, the electromotive force Vref, the pump current Ip0s, the pump current Ip0, the pump current Ip1, and the pump current Ip2. The electromotive force V0 is detected by the oxygen partial pressure detection sensor cell 80 for controlling the main pump. The electromotive force V1 is detected by the oxygen partial pressure detection sensor cell 81 for controlling the auxiliary pump. The electromotive force V2 is detected by the oxygen partial pressure detection sensor cell 82 for controlling the measurement pump. The electromotive force Vref is detected by the sensor cell 83. The pump current Ip0s is detected by the preliminary pump cell 15. The pump current Ip0 is detected by the main pump cell 21. The pump current Ip1 is detected by the auxiliary pump cell 50. The pump current Ip2 is detected by the measurement pump cell 41. Furthermore, the controller 90 outputs control signals to the variable power supply 17 of the preliminary pump cell 15, the variable power supply 24 of the main pump cell 21, the variable power supply 52 of the auxiliary pump cell 50, and the variable power supply 46 of the measurement pump cell 41.

The controller 90 feedback-controls the voltage Vp0s of the variable power supply 17 in a manner such that the pump current Ip0s of the preliminary pump cell 15 reaches a target value Ip0s*. The controller 90 controls the voltage Vp0s in a manner such that oxygen is pumped into the buffer space 12 and does not control the voltage Vp0s in a manner such that oxygen is pumped from the buffer space 12. Furthermore, in the present embodiment, for the controller 90, the target value Ip0s* is set to a constant value. The target value Ip0s* is set to a value such that, even in a case where a measurement-object gas outside of the sensor element 101 is a low-oxygen atmosphere (e.g., atmosphere having an oxygen concentration less than or equal to 0.1 vol %, less than 0.2 vol %, less than 1 vol %, or the like), the measurement-object gas after oxygen is pumped to the inside by the preliminary pump cell 15 (i.e., the measurement-object gas to be introduced into the first internal space 20) is not a low-oxygen atmosphere. It is to be noted that, in a case where the air-fuel ratio of the measurement-object gas is lower than the stoichiometric air-fuel ratio, that is, the measurement-object gas is a rich atmosphere, unburned fuel is included in the measurement-object gas, and therefore, the oxygen concentration can be determined by the amount of oxygen necessary to sufficiently combust the fuel. In this case, the oxygen concentration is expressed as a negative value. Accordingly, the target value Ip0s* is set in the following manner, for example. First, a minimum oxygen concentration of exhaust gases from an internal combustion engine that uses the gas sensor 100 is investigated in advance. The minimum oxygen concentration is a minimum among oxygen concentrations in various operation conditions (in some cases, the oxygen concentration may decrease to a negative value). Subsequently, the target value Ip0s* is set based on the amount of oxygen necessary to increase the minimum oxygen concentration of the measurement-object gas to an oxygen concentration higher than the oxygen concentration of a low-oxygen atmosphere (e.g. oxygen concentration greater than 0.1 vol %, greater than or equal to 0.2 vol %, greater than or equal to 1 vol %, or the like). Since the target value Ip0s* is set to a constant value, the controller 90 controls the preliminary pump cell 15 in a manner such that a constant flow rate of oxygen is pumped into the buffer space 12. The value of the target value Ip0s* may be appropriately set based on an experiment as described above. For example, the target value Ip0s* may be 0.5 mA or greater and 3 mA or less.

The controller 90 feedback-controls the pump voltage Vp0 of the variable power supply 24 in a manner such that the electromotive force V0 reaches a target value (referred to as a "target value V0*") (i.e., in a manner such that the oxygen concentration in the first internal space 20 becomes a constant target concentration). Accordingly, the pump current Ip0 changes in accordance with the concentration of oxygen present in the measurement-object gas and the flow rate of oxygen being pumped to the inside by the preliminary pump cell 15.

Furthermore, the controller 90 feedback-controls the voltage Vp1 of the variable power supply 52 in a manner such that the electromotive force V1 reaches a constant value (referred to as "target value V1*") (i.e., in a manner such that the oxygen concentration in the second internal space 40 becomes a predetermined low-oxygen concentration that has substantially no influence on the measurement of NOx). In addition, the controller 90 sets (feedback-controls) the target value V0* of the electromotive force V0 based on the pump current Ip1 in a manner such that the pump current Ip1, which flows due to the voltage Vp1, reaches a constant value (referred to as a "target value Ip1*"). As a result, the gradient of the partial pressure of oxygen present in the measurement-object gas to be introduced into the second internal space 40 through the third diffusion-rate-limiting portion 30 is consistently a constant gradient. Furthermore, the partial pressure of oxygen present in the atmosphere of the second internal space 40 is controlled to a low partial pressure that has substantially no influence on the measurement of NOx.

Further, the controller 90 feedback-controls the voltage Vp2 of the variable power supply 46 in a manner such that the electromotive force V2 reaches a constant value (referred to as a "target value V2*") (i.e., in a manner such that the oxygen concentration in the third internal space 61 becomes a predetermined low concentration). Accordingly, oxygen is pumped from the third internal space 61 in a manner such that the amount of oxygen, which is produced when NOx in the measurement-object gas is reduced in the third internal space 61, becomes substantially zero. Subsequently, the controller 90 obtains the pump current Ip2 and, based on the pump current Ip2, calculates the concentration of NOx present in the measurement-object gas. The pump current Ip2 is a detection value corresponding to the oxygen produced in the third internal space 61, the oxygen being oxygen derived from a specific gas (in this case, NOx).

A relationship formula representing a relationship between the pump current Ip2 and the concentration of NOx is stored in the memory 94. The relationship formula may be, for example, a linear function formula. The relationship formula can be determined by experimentation in advance.

An example of usage of the gas sensor 100, which is configured as described above, will be described below. Assume that the CPU 92 of the controller 90 is in a state in which the CPU 92 is controlling the above-described pump cells 15, 21, 41, and 50 and obtaining the voltages V0, V1, V2, and Vref from the above-described sensor cells 80 to 83. In this state, when the measurement-object gas is introduced through the gas inlet port 10, the measurement-object gas, first, passes through the first diffusion-rate-limiting portion 11 and is then introduced into the buffer space 12, and, in the buffer space 12, oxygen is pumped into the measurement-object gas by the preliminary pump cell 15. Thereafter, the measurement-object gas, which contains the pumped oxygen, reaches the first internal space 20. Next, in the first internal space 20 and the second internal space 40, the oxygen concentration of the measurement-object gas is adjusted by the main pump cell 21 and the auxiliary pump cell 50, and the adjusted measurement-object gas reaches the third internal space 61. Subsequently, based on the obtained pump current Ip2 and the relationship formula stored in the memory 94, the CPU 92 detects the concentration of NOx present in the measurement-object gas.

Thus, oxygen is pumped into the buffer space 12 by the preliminary pump cell 15 for the purpose of, as described above, suppressing the measurement-object gas from being introduced into the first internal space 20 in a state in which the measurement-object gas is a low-oxygen atmosphere. Reasons for doing this will be described. The present inventors investigated pump currents Ip0 and pump currents Ip2 obtained by varying the value of the oxygen concentration of the measurement-object gas and the value of the target value Ip0s*. The measurement-object gas was a gas before being introduced into the gas inlet port 10. The measurement-object gas used was an adjusted model gas. In the model gas, the base gas was nitrogen, the specific gas component was 500 ppm NO, and the fuel gas was 1000 ppm carbon monoxide gas and 1000 ppm ethylene gas. The model gas was adjusted such that the water concentration was 5 vol % and the oxygen concentration was 0.005 to 20 vol %. The temperature of the model gas was 250° C., and the model gas was flowed through a pipe having a diameter of 20 mm at a flow rate of 50 L/min. It should be noted that, in the gas sensor used in this investigation (hereinafter referred to as a "gas sensor of Reference Example"), the preliminary pump electrode 16 and the inner pump electrode 22 contained Au as with the auxiliary pump electrode 51. Except for this feature, the gas sensor of Reference Example is the same as the gas sensor 100 of the present embodiment.

Figure 3:
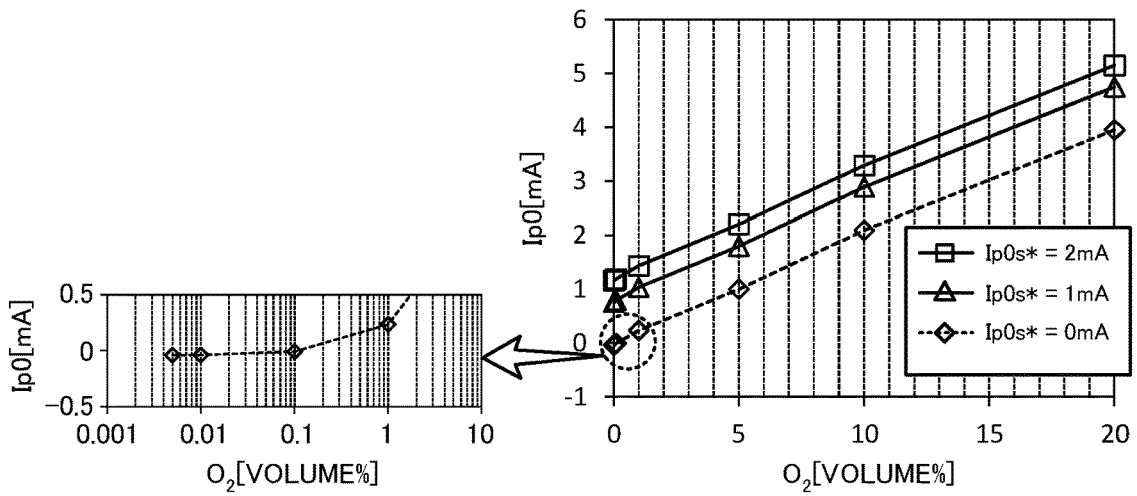
FIG. 3 is a graph illustrating a relationship between the oxygen concentration of a measurement-object gas and a pump current Ip0.
Figure 4:
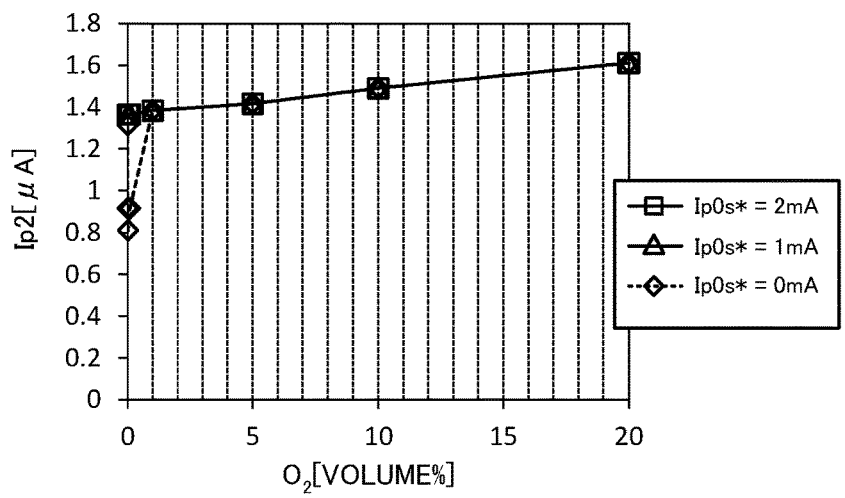
FIG. 4 is a graph illustrating a relationship between the oxygen concentration of a measurement-object gas and a pump current Ip2.
Figure 5:
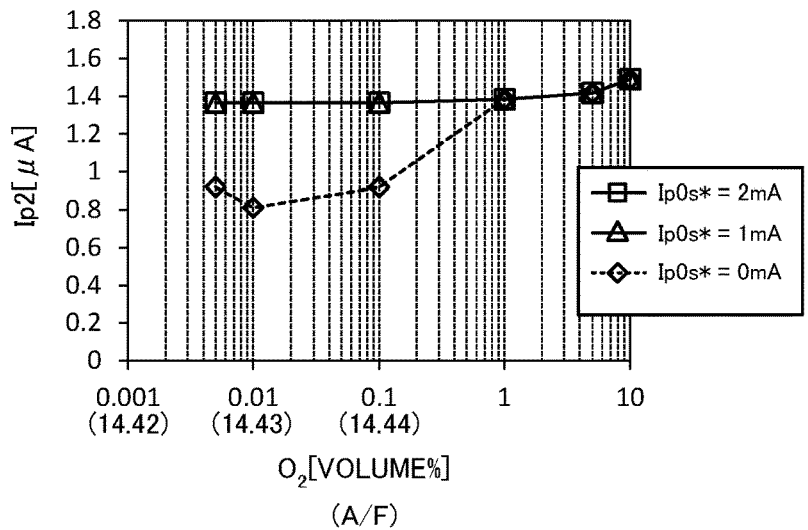
FIG. 5 is a graph illustrating in enlarged view a region of FIG. 4 corresponding to oxygen concentrations of 10 vol % or less.

FIG. 3 is a graph illustrating a relationship between the oxygen concentration of a measurement-object gas and the pump current Ip0. FIG. 3 illustrates cases in which the target value Ip0s* was 0 mA, the target value Ip0s* was 1 mA, and the target value Ip0s* was 2 mA. The left graph of FIG. 3 is an enlarged view of the portion of the right graph of FIG. 3 encircled by a dashed line (in the left graph, the horizontal axis is on a log scale). FIG. 4 is a graph illustrating a relationship between the oxygen concentration of a measurement-object gas and the pump current Ip2. FIG. 4 shows the same cases as those in FIG. 3. FIG. 5 is a graph illustrating in enlarged view a region of FIG. 4 corresponding to oxygen concentrations of 10 vol % or less. In FIG. 5, the horizontal axis is on a log scale. The oxygen concentration on the horizontal axis is the oxygen concentration of the adjusted model gas, that is, the oxygen concentration of a measurement-object gas that is outside of the sensor element 101. Furthermore, the A/F of the model gas is also shown in parenthesis on the horizontal axis of FIG. 5. The A/F is a value measured by using a MEXA-730λ, which is manufactured by HORIBA, Ltd.

As can be seen from FIGS. 4 and 5, in the case where the oxygen concentration of the model gas was greater than or equal to 1 vol %, the values of pump currents Ip2 corresponding to the same oxygen concentration were substantially the same in all of the cases in which the target value Ip0s* was 0 mA, the target value Ip0s* was 1 mA, and the target value Ip0s* was 2 mA. In contrast, in the case where the oxygen concentration of the model gas was less than or equal to 0.1 vol %, a pump current Ip2 generated in a case where the target value Ip0s* was 0 mA, that is, the preliminary pump cell 15 did not pump oxygen to the inside at all, had a value smaller than a pump current Ip2 generated in a case where the preliminary pump cell 15 pumped oxygen to the inside. That is, the sensitivity of the pump current Ip2 to the concentration of NOx was decreased.

FIG. 3 confirms that, even when the values of the oxygen concentrations of the model gases are the same, the greater the target value Ip0s*, the greater the pump current Ip0. However, with regard to the amount of increase in the pump current Ip0, which was determined in comparison with the pump current Ip0 obtained in a case where the target value Ip0s* was 0 mA, the pump current Ip0 obtained in a case where the target value Ip0s* was 2 mA was not equal to twice the pump current Ip0 obtained in a case where the target value Ip0s* was 1 mA. That is, the amount of increase in the pump current Ip0 was not directly proportional to the target value Ip0s*. The reason for this is believed to be that, even when the target value Ip0s* is large, some of the oxygen pumped into the buffer space 12 escapes through the gas inlet port 10 to the outside as a result of diffusion, and therefore not all of the pumped oxygen reaches the first internal space 20. Furthermore, FIG. 3 shows that the pump current Ip0 had a negative value only in cases where Ip0s* is 0 mA and the concentration of the model gas was less than or equal to 0.1 vol % (cases shown on the left side of FIG. 3, in which the oxygen concentration was 0.005 vol %, 0.01 vol %, or 0.1 vol %). Thus, FIGS. 3 to 5 confirm that the sensitivity of the pump current Ip2 was low when the pump current Ip0 had a negative value. Negative values of the pump current Ip0 mean that the main pump cell 21 is pumping oxygen into the first internal space 20 (pumping oxygen in a manner such that the oxygen partial pressure in the first internal space 20 reaches the target value V0*), not pumping oxygen from the first internal space 20. That is, negative values of the pump current Ip0 mean that the oxygen concentration of the measurement-object gas to be introduced into the first internal space 20 is lower than the oxygen concentration represented by the target value V0*.

The results described above demonstrate that a specific gas measurement accuracy decreases in a case where the oxygen concentration of the measurement-object gas to be introduced into the first internal space 20 is low. In contrast, in the case where the preliminary pump cell 15 is operated, the measurement-object gas, after oxygen is supplied by the preliminary pump cell 15, is introduced into the first internal space 20 as described above, and consequently, as illustrated in FIG. 3, the value of Ip0 can be increased (i.e., the oxygen concentration of the measurement-object gas to be introduced into the first internal space 20 can be increased). As a result, it is unlikely that the measurement-object gas will reach the first internal space 20 in a state in which the measurement-object gas is a low-oxygen atmosphere, and consequently, a decrease in measurement accuracy that may occur in the case where the measurement-object gas is a low-oxygen atmosphere is suppressed. From the results in FIGS. 3 to 5, it is believed that, when the preliminary pump cell 15 pumps oxygen into the buffer space 12 in a manner such that a measurement-object gas having an oxygen concentration less than or equal to 0.1 vol % does not reach the first internal space 20, that is, the oxygen concentration of the measurement-object gas reaching the first internal space 20 is greater than 0.1 vol %, a decrease in measurement accuracy can be suppressed. Furthermore, it is believed that the preliminary pump cell 15 is to be operated in a manner such that the oxygen concentration of the measurement-object gas reaching the first internal space 20 is preferably greater than or equal to 0.2 vol % and is more preferably greater than or equal to 1 vol %.

In the case where the preliminary pump cell 15 does not pump oxygen to the inside, a measurement accuracy decreases when the measurement-object gas is a low-oxygen atmosphere. The reason for this is unknown, but, for example, may be as follows. One possible reason is that, when a measurement-object gas that is a low-oxygen atmosphere is introduced into the first internal space 20, the inner pump electrode 22 acts as a catalyst to cause NOx to be reduced in the first internal space 20 before the measurement-object gas reaches the third internal space 61. Another possible reason is as follows. In the case where the measurement-object gas is a rich atmosphere, unburned components such as a hydrocarbon (HC) and carbon monoxide exist in the measurement-object gas. NOx can react with the components, and therefore NOx tends to be reduced in the first internal space 20. For example, in the instance of a gasoline engine, the air-fuel ratio of the measurement-object gas remains at or near the stoichiometric air-fuel ratio in many cases, and therefore the measurement-object gas may be consistently a low-oxygen atmosphere. Even in such a case, the specific gas concentration can be detected accurately as long as oxygen is pumped to the inside by the preliminary pump cell 15. Furthermore, the controller 90 feedback-controls the target value V0* in a manner such that the pump current Ip1 reaches a constant value. Possibly, this may also be related to a decrease in measurement accuracy that may occur when the measurement-object gas is a low-oxygen atmosphere. For example, in a case where the oxygen concentration of the measurement-object gas to be introduced into the first internal space 20 is temporarily decreased, there is a time lag before the second internal space 40 is affected by the influence. Accordingly, there is a time lag before the target value V0* is changed based on the pump current Ip1 to an appropriate value, and as a result, a phenomenon in which, temporarily, oxygen in the first internal space 20 is pumped to the outside excessively may occur. Thus, it is possible that, in the case where the oxygen concentration in the first internal space 20 decreases excessively as a result of the phenomenon, reduction of NOx may occur in the first internal space 20. In contrast, in the case where the preliminary pump cell 15 is operated, it is believed that a decrease in measurement accuracy is suppressed for the following reason: since oxygen is supplied by the preliminary pump cell 15, the oxygen concentration in the first internal space 20 does not decrease to such an extent that NOx is reduced in the first internal space 20, even when a temporary decrease in the oxygen concentration of the measurement-object gas, as described above, occurs.

Figure 6:
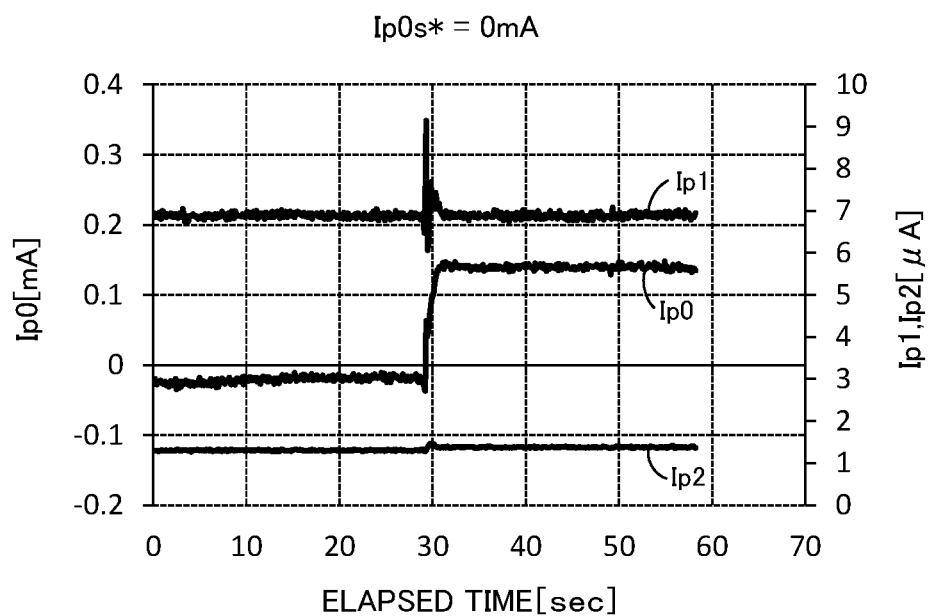
FIG. 6 is a graph illustrating temporal changes in the pump current in a case where a target value Ip0s* is 0 mA.
Figure 7:
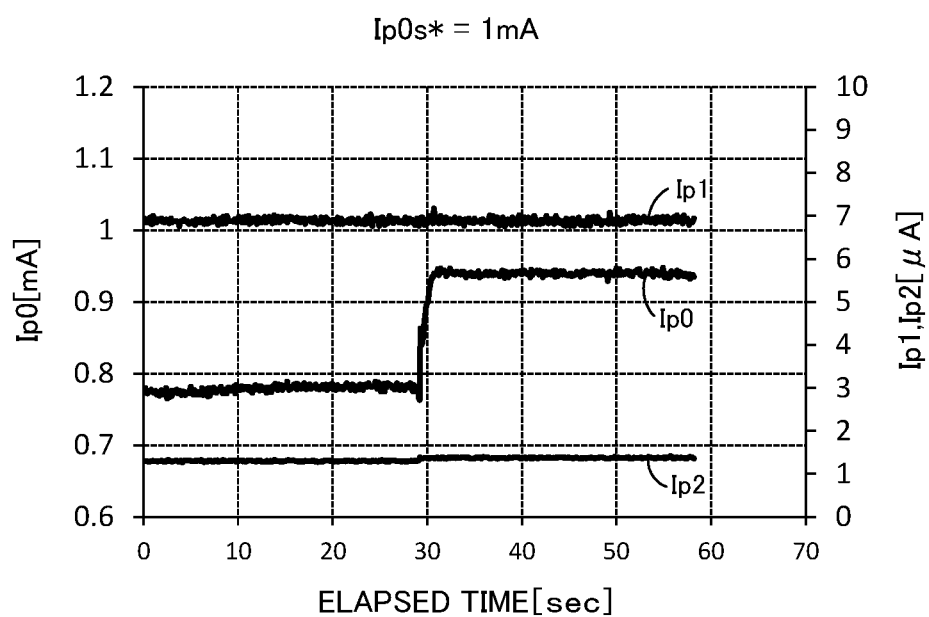
FIG. 7 is a graph illustrating temporal changes in the pump current in a case where the target value Ip0s* is 1 mA.

Furthermore, in the gas sensor 100 of the present embodiment, spike noise in the pump current Ip1 and the pump current Ip2, which occurs when the atmosphere of the measurement-object gas suddenly changes from a rich atmosphere to a lean atmosphere, or vice versa, can be suppressed. By using the above-described gas sensor of Reference Example, the present inventors investigated the behavior of pump currents Ip0, Ip1, and Ip2, which were generated when a measurement-object gas to be introduced into the gas inlet port 10 was suddenly changed from a rich atmosphere to a lean atmosphere. The measurement-object gases used were adjusted model gases. The following model gases were prepared: a rich-atmosphere gas having an oxygen concentration of 0.05 vol % and a lean-atmosphere gas having an oxygen concentration of 0.65 vol %. When 30 seconds had passed after the rich-atmosphere gas started to flow through a pipe, the rich-atmosphere gas was replaced with the lean-atmosphere gas. The conditions for the model gases except for the oxygen concentration were the same as those for the model gas used in the measurement associated with FIGS. 3 to 5. Note that the model gas contains fuel gases (1000 ppm carbon monoxide gas and 1000 ppm ethylene gas) as described above, and therefore a model gas having an oxygen concentration of 0.05 vol % is a rich atmosphere. FIG. 6 is a graph illustrating temporal changes in the pump currents Ip0, Ip1, and Ip2 in a case where the target value Ip0s* is 0 mA. FIG. 7 is a graph illustrating temporal changes in the pump currents Ip0, Ip1, and Ip2 in a case where the target value Ip0s* is 1 mA.

As can be seen from FIGS. 6 and 7, in the case where the target value Ip0s* was 1 mA (FIG. 7), unlike the case of FIG. 6, the pump current Ip0 did not decrease to a negative value and consistently had a positive value even in the time period during which the measurement-object gas was a rich atmosphere (elapsed time was 0 to 30 seconds). Furthermore, in FIG. 7, the spike noise in the pump currents Ip1 and Ip2, which occurred when the rich atmosphere was changed to the lean atmosphere, was reduced compared with FIG. 6. This is believed to be because spike noise tends to occur in the pump currents Ip1 and Ip2 when the pump current Ip0 changes from positive to negative or vice versa. For example, in the instance of a gasoline engine, the air-fuel ratio of the measurement-object gas remains at or near the stoichiometric air-fuel ratio in many cases, and therefore, if the preliminary pump cell 15 does not pump oxygen into the buffer space 12, the pump current Ip0 may frequently change between positive and negative, and consequently spike noise may frequently occur. In the gas sensor 100 of the present embodiment, such changes in the pump current Ip0 between positive and negative can be suppressed from occurring.

It is to be noted that, in the above-described gas sensor of Reference Example, the preliminary pump electrode 16, the inner pump electrode 22, and the auxiliary pump electrode 51 each contain Au. The present inventors prepared gas sensors of Experimental Examples 1 to 8, in which the presence or absence of Au in each of the electrodes was varied as shown in Table 1. For all of Experimental Examples 1 to 8, the preliminary pump electrode 16, the inner pump electrode 22, and the auxiliary pump electrode 51 were each a porous cermet electrode containing one or more noble metals and $ZrO_2$. In Table 1, the value "0.8" means that the electrode contains Pt and Au as noble metals, and that the mass percentage of Au relative to Pt in the electrode is 0.8 wt %. In Table 1, the symbol "-" means that the electrode contains Pt exclusively as a noble metal without containing Au.

TABLE 1

| | Mass percentage of Au relative to Pt in the electrode [wt %] | | |
|---|---|---|---|
| | PRELIMINARY PUMP ELECTRODE | INNER PUMP ELECTRODE | AUXILIARY PUMP ELECTRODE |
| EXPERIMENTAL EXAMPLE 1 | 0.8 | 0.8 | 0.8 |
| EXPERIMENTAL EXAMPLE 2 | — | 0.8 | 0.8 |
| EXPERIMENTAL EXAMPLE 3 | 0.8 | — | — |
| EXPERIMENTAL EXAMPLE 4 | — | — | — |
| EXPERIMENTAL EXAMPLE 5 | 0.8 | — | 0.8 |
| EXPERIMENTAL EXAMPLE 6 | — | — | 0.8 |
| EXPERIMENTAL EXAMPLE 7 | 0.8 | 0.8 | — |
| EXPERIMENTAL EXAMPLE 8 | — | 0.8 | — |

With regard to each of the gas sensors of Experimental Examples 1 to 8, the relationship between the specific gas concentration in the measurement-object gas and the pump current Ip2, with the target value Ip0s* being 1 mA, was investigated. The measurement-object gases used were adjusted three types of model gases. In the model gases, the specific gas component was NO, and the NO concentration was as follows: 0 ppm, 250 ppm, and 500 ppm. In each of the three types of model gases, the base gas was nitrogen, and the water concentration was adjusted to 3 vol % and the oxygen concentration was adjusted to 1 vol %. The temperature of the model gases was 250° C., and the model gases were flowed through a pipe having a diameter of 20 mm at a flow rate of 50 L/min. Table 2 and FIG. 8 show a relationship between the NO concentration and the pump current Ip2 regarding the gas sensors of Experimental Examples 1 to 8.

TABLE 2

| NO CONCEN- TRATION [ppm] | PUMP CURRENT Ip2[μA] | | | | | | | |
|---|---|---|---|---|---|---|---|---|
| | EXPERI- MENTAL EXAMPLE 1 | EXPERI- MENTAL EXAMPLE 2 | EXPERI- MENTAL EXAMPLE 3 | EXPERI- MENTAL EXAMPLE 4 | EXPERI- MENTAL EXAMPLE 5 | EXPERI- MENTAL EXAMPLE 6 | EXPERI- MENTAL EXAMPLE 7 | EXPERI- MENTAL EXAMPLE 8 |
| 0 | 0.09 | 0.09 | 0.09 | 0.08 | 0.08 | 0.08 | 0.08 | 0.09 |
| 250 | 0.76 | 0.76 | 0.09 | 0.08 | 0.76 | 0.75 | 0.08 | 0.09 |
| 500 | 1.43 | 1.43 | 0.09 | 0.08 | 1.43 | 1.43 | 0.08 | 0.09 |

Figure 8:
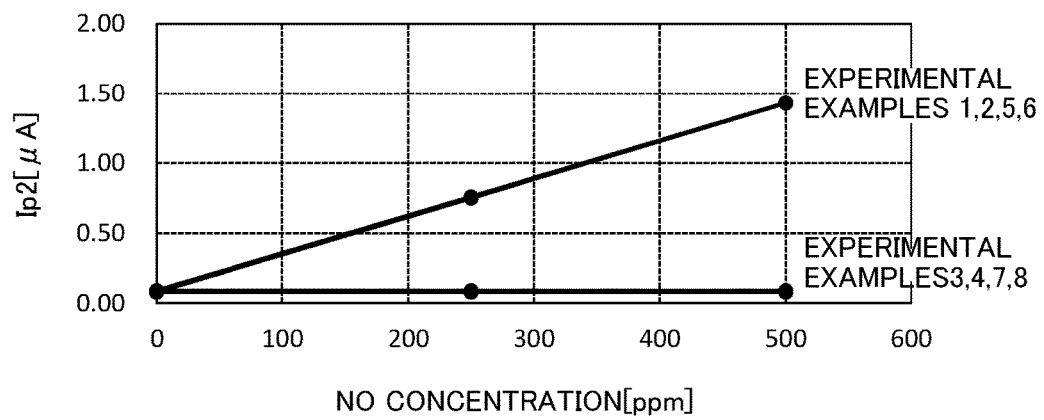
FIG. 8 is a graph illustrating a relationship between a NO concentration and the pump current Ip2 regarding gas sensors of Experimental Examples 1 to 8.

The results shown in Table 2 and FIG. 8 indicate that, in Experimental Examples 3, 4, 7, and 8, in each of which the auxiliary pump electrode 51 did not contain Au, there was substantially no change in the pump current Ip2 even with the changes in the NO concentration, and the pump current Ip2 was substantially 0 μA. This is believed to be because No was reduced before reaching the measurement electrode 44 as a result of the catalytic activity of the auxiliary pump electrode 51. In contrast, in Experimental Examples 1, 2, 5, and 6, in each of which the auxiliary pump electrode 51 contained Au, there was a linear relationship between the NO concentration and the pump current Ip2. Furthermore, in Experimental Examples 1, 2, 5, and 6, the values of pump currents Ip2 corresponding to each of the NO concentrations were substantially equal to each other. That is, whether or not the preliminary pump electrode 16 contained Au and whether or not the inner pump electrode 22 contained Au had no influence on the pump current Ip2. This result indicates the following. It is sufficient that the auxiliary pump electrode 51 contain Au. In the preliminary pump electrode 16 and the inner pump electrode 22, inclusion of Au is not necessary. Even without the presence of Au, no reduction of NO due to the preliminary pump electrode 16 or the inner pump electrode 22 occurs. From this result, the present inventors found that, when the preliminary pump cell 15 is configured to pump oxygen to the inside, at least one of the preliminary pump electrode 16 and the inner pump electrode 22 does not need to contain Au. Based on this result, the gas sensor 100 of the present embodiment is configured as follows: at least one of the preliminary pump electrode 16 and the inner pump electrode 22 contains no Au, whereas the auxiliary pump electrode 51 contains Au. That is, each of Experimental Examples 2, 5, and 6 corresponds to the gas sensor 100 of the present embodiment and therefore corresponds to examples of the gas sensor of the present invention. Each of Experimental Examples 1, 3, 4, 7, and 8 corresponds to a comparative example of the present invention.

The reason for the above result is believed to be as follows. First, during use of the gas sensor 100, the preliminary pump cell 15, under control of the CPU 92 as described above, supplies oxygen to the measurement-object gas, which is a measurement-object gas before the adjustment of the oxygen concentration by the main pump cell 21 and the auxiliary pump cell 50. As such, the preliminary pump cell 15 pumps oxygen to the inside, whereas the main pump cell 21 and the auxiliary pump cell 50 pump oxygen to the outside. Accordingly, the magnitude relationship between the oxygen concentrations in vicinities of the electrodes in the measurement-object gas flow section is believed to be as follows: (vicinity of preliminary pump electrode 16)≥(vicinity of inner pump electrode 22)>(vicinity of auxiliary pump electrode 51)>(vicinity of measurement electrode 44). That is, even in a case where the measurement-object gas is a low-oxygen atmosphere before the measurement-object gas is introduced into the measurement-object gas flow section, the oxygen concentrations in vicinities of the preliminary pump electrode 16 and the inner pump electrode 22 are maintained at high oxygen concentrations compared with a vicinity of the auxiliary pump electrode 51. Further, the higher the oxygen concentration, the less likely it is that reduction of NOx will occur. Thus, even in the case where at least one of the preliminary pump electrode 16 and the inner pump electrode 22 contains no noble metal (in this case, Au) having a catalytic activity suppression ability, it is unlikely that reduction of NOx due to the electrode will occur. On the other hand, the measurement-object gas reaches a vicinity of the auxiliary pump electrode 51 after oxygen is pumped to the outside by the main pump cell 21. As a result, in a vicinity of the pump electrode 51, reduction of NOx due to the auxiliary pump electrode 51 can easily occur. However, the auxiliary pump electrode 51 contains Au and therefore can suppress NOx from being reduced. As is clear from the above description, in the gas sensor 100 of the present embodiment, reduction of NOx before NOx reaches the measurement electrode 44 is sufficiently suppressed from occurring, and therefore a specific gas concentration detection accuracy is sufficient.

Furthermore, in a case where both the preliminary pump electrode 16 and the inner pump electrode 22 contain Au, Au may adhere to the measurement electrode 44 as a result of evaporation from the electrodes in association with the use of the gas sensor 100. When Au adheres to the measurement electrode 44, the catalytic activity of the measurement electrode 44 is suppressed, and consequently, NOx is not reduced sufficiently in a vicinity of the measurement electrode 44. As a result, the actual pump current Ip2 is decreased compared with the correct pump current Ip2, which corresponds to the concentration of NOx. Consequently, a specific gas concentration detection accuracy decreases. In contrast, in the gas sensor 100 of the present embodiment, at least one of the preliminary pump electrode 16 and the inner pump electrode 22 contains no noble metal having a catalytic activity suppression ability, and therefore, noble metal evaporation in association with the use of the gas sensor 100 is suppressed, and a decrease in detection accuracy in association with the use is suppressed.

As is clear from the above description, the gas sensor 100 of the present embodiment has a specific gas concentration detection accuracy that is maintained over a long period of time. In contrast, for example, in a case where the auxiliary pump electrode 51 also contains no Au as in Experimental Examples 3, 4, 7, and 8, a specific gas concentration detection accuracy is already low at the beginning of the use of the gas sensor. Furthermore, for example, in a case where both the preliminary pump electrode 16 and the inner pump electrode 22 contain Au as in Experimental Example 1, a specific gas concentration detection accuracy tends to decrease in association with the use of the gas sensor. That is, the durability of the gas sensor decreases.

Note that, although the auxiliary pump electrode 51 contains Au, Au in the auxiliary pump electrode 51 has a relatively low tendency to evaporate. This will be described. The tendency for Au to evaporate from an electrode as described above increases as the oxygen concentration increases. For example, in an electrode containing Pt and Au, Pt is more likely to be oxidized to form $PtO_2$ as the oxygen concentration increases. $PtO_2$ has a saturated vapor pressure higher than that of Pt and therefore evaporates more easily than Pt. Further, when Pt becomes $PtO_2$ and evaporates, the remaining Au also tends to evaporate. This is because elemental Au has a higher saturated vapor pressure than a Pt—Au alloy. On the contrary, since the oxygen concentration in a vicinity of the auxiliary pump electrode 51 is low as described above, Au in the auxiliary pump electrode 51 has a relatively low tendency to evaporate. Hence, even in the case where the auxiliary pump electrode 51 contains Au, a decrease in detection accuracy in association with the use of the gas sensor 100 as described above is unlikely to occur.

It is preferable that neither the preliminary pump electrode 16 nor the inner pump electrode 22 contain a noble metal having a catalytic activity suppression ability. With this configuration, evaporation of a noble metal having a catalytic activity suppression ability is further suppressed. As a result, the effect of maintaining a specific gas concentration detection accuracy over a long period of time is enhanced.

Here, correspondence relationships between constituent elements of the present embodiment and constituent elements of the present invention will be clarified. The layered body of the present embodiment in which six layers, namely the first substrate layer 1, the second substrate layer 2, the third substrate layer 3, the first solid electrolyte layer 4, the spacer layer 5, and the second solid electrolyte layer 6 are layered in this order corresponds to the element body of the present invention. The buffer space 12 corresponds to the preliminary chamber. The preliminary pump cell 15 corresponds to the preliminary pump cell. The first internal space 20 corresponds to the first internal space. The main pump cell 21 corresponds to the main pump cell. The second internal space 40 corresponds to the second internal space. The auxiliary pump cell 50 corresponds to the auxiliary pump cell. The third internal space 61 corresponds to the measurement chamber. The measurement electrode 44 corresponds to the measurement electrode. The reference electrode 42 corresponds to the reference electrode. The oxygen partial pressure detection sensor cell 82 for controlling the measurement pump corresponds to the measurement voltage detection device. The pump current Ip2 corresponds to the detection value. The CPU 92 of the controller 90 corresponds to the specific gas concentration detection device. The preliminary pump electrode 16 corresponds to the inner preliminary pump electrode. The inner pump electrode 22 corresponds to the inner main pump electrode. The auxiliary pump electrode 51 corresponds to the inner auxiliary pump electrode. Furthermore, the pump current Ip0s corresponds to the preliminary pump current. The CPU 92 corresponds to the preliminary pump control device. The memory 94 corresponds to the storage device. The pump current Ip0 corresponds to the pump current of the main pump cell. The CPU 92 corresponds to the oxygen concentration detection device. The outer pump electrode 23 corresponds to the measurement-object gas-side electrode.

In the gas sensor 100 of the present embodiment described above, the preliminary pump cell 15 supplies oxygen to the measurement-object gas before the oxygen concentration is adjusted by the main pump cell 21, and as a result, a vicinity of the preliminary pump electrode 16 and a vicinity of the inner pump electrode 22 are prevented from becoming a low-oxygen atmosphere even in the case where the measurement-object gas before being introduced into the measurement-object gas flow section is a low-oxygen atmosphere. As a result, even in the case where at least one of the preliminary pump electrode 16 and the inner pump electrode 22 contains no noble metal (e.g., Au) having a catalytic activity suppression ability, reduction of a specific gas due to the electrode is unlikely to occur. Furthermore, since at least one of the preliminary pump electrode 16 and the inner pump electrode 22 contains no noble metal having a catalytic activity suppression ability, an instance in which noble metal evaporates in association with the use of the gas sensor 100 and adheres to the measurement electrode 44 is suppressed from occurring. Accordingly, the gas sensor 100 has a specific gas concentration detection accuracy that is maintained over a long period of time.

Furthermore, the CPU 92 controls the preliminary pump cell 15 in a manner such that a constant preliminary pump current (target value Ip0s*) flows, and therefore, with a relatively simple control, oxygen can be supplied to a measurement-object gas that is a low-oxygen atmosphere, in the buffer space 12.

In addition, the CPU 92 detects the specific gas concentration by using a common relationship formula stored in the memory 94 regardless of whether a measurement-object gas outside of the element body is a low-oxygen atmosphere. As described with reference to FIGS. 4 and 5, in the gas sensor 100 of the present embodiment, the sensitivity of the pump current Ip2 tends not to decrease even in the case where the measurement-object gas is a low-oxygen atmosphere. Hence, the gas sensor 100 can detect the specific gas concentration accurately without using different relationship formulas for the case in which the measurement-object gas is a low-oxygen atmosphere and for the case in which the measurement-object gas is not a low-oxygen atmosphere. Hence, the gas sensor 100 can detect the specific gas concentration readily and accurately.

In addition, the preliminary pump cell 15 pumps oxygen into the buffer space 12 from a vicinity of the outer pump electrode 23. With this configuration, the following is possible. In comparison with, for example, a case in which oxygen is pumped into the buffer space 12 from a vicinity of the reference electrode 42, a decrease in measurement accuracy that may occur when the potential of the reference electrode 42 changes as a result of a voltage drop due to the current during pumping is suppressed.

Note that the present invention is in no way limited to the embodiment described above and may be implemented in a variety of embodiments that fall within the technical scope of the present invention.

For example, in the embodiment described above, the CPU 92 detects the specific gas concentration based on the pump current Ip2 and a relationship formula representing a relationship between the pump current Ip2 and the concentration of NOx stored in the memory 94, but this configuration is non-limiting. For example, the CPU 92 may detect the specific gas concentration corrected based on the oxygen concentration of a measurement-object gas that is outside of the sensor element 101. For example, referring to FIG. 5, according to the data in which the target value Ip0s* is 1 mA or 2 mA, in the case where the oxygen concentration of the measurement-object gas is consistently less than or equal to 5%, the value of the pump current Ip2 does not significantly change even when the oxygen concentration changes, provided that the actual concentration (real concentration) of a specific gas is uniform (see FIG. 5). On the other hand, in the case where the oxygen concentration of the measurement-object gas may change over a larger range, the pump current Ip2 may change with the oxygen concentration, as illustrated in FIG. 4. In a case where the pump current Ip2 changes with the oxygen concentration relatively significantly as just described, the CPU 92 may detect the specific gas concentration with a correction based on the oxygen concentration. This improves a specific gas concentration measurement accuracy. For example, referring to FIG. 4, according to the data in which the target value Ip0s* is 1 mA or 2 mA, the pump current Ip2 linearly changes with the oxygen concentration when the specific gas concentration is uniform, and therefore the relationship between the oxygen concentration and the pump current Ip2 can be approximated with a linear function. Accordingly, by using the linear function formula (relationship formula for correction), the CPU 92 may derive a corrected pump current by excluding an influence of the oxygen concentration from the pump current Ip2, which is obtained from the measurement pump cell 41, and, based on the corrected pump current and the relationship formula stored in the memory 94 in the embodiment described above, the CPU 92 may detect the specific gas concentration. In this case, the memory 94 may also store the relationship formula for correction. Alternatively, in place of the relationship formula stored in the memory 94 in the embodiment described above, a relationship formula in which the relationship formula for correction is taken into account, that is, a relationship formula representing a relationship between the pump current Ip2, the specific gas concentration, and the oxygen concentration of a measurement-object gas outside of the sensor element 101 may be stored, and, by using this relationship formula, the CPU 92 may detect a corrected a specific gas concentration. As with the relationship formula stored in the memory 94 in the embodiment described above, with regard to the relationship formula for correction and the relationship formula in which the relationship formula for correction is taken into account, too, the specific gas concentration can be detected accurately by using the formula, which is a common formula, regardless of whether a measurement-object gas outside of the sensor element 101 is a low-oxygen atmosphere.

In the case where the CPU 92 performs correction as described above, the CPU 92 may detect the oxygen concentration of the measurement-object gas that is outside of the sensor element 101. It is to be noted that the constant pump current Ip0s (i.e., target value Ip0s*) corresponds to the flow rate of oxygen pumped into the buffer space 12 by the preliminary pump cell 15. Furthermore, the pump current Ip0 corresponds to the flow rate of oxygen pumped from the first internal space 20. Hence, based on the pump current Ip0s, the pump current Ip0, and the target concentration of the oxygen concentration in the first internal space 20, the CPU 92 can detect the oxygen concentration of a measurement-object gas that is a gas before the preliminary pump cell 15 pumps oxygen to the inside and the main pump cell 21 pumps oxygen to the outside. That is, the CPU 92 can detect the oxygen concentration of the measurement-object gas that is outside of the sensor element 101. Accordingly, the oxygen concentration necessary for the correction can be detected by the gas sensor 100. In addition, the CPU 92 can also detect the oxygen concentration of the measurement-object gas that is outside of the sensor element 101 based on, for example, a voltage Vref between the reference electrode 42 and the outer pump electrode 23. Alternatively, the CPU 92 may obtain the oxygen concentration of the measurement-object gas that is outside of the sensor element 101 from a device other than the gas sensor 100, such as a different sensor or the ECU of the engine, and may use the oxygen concentration for the correction.

In the embodiment described above, the preliminary pump cell 15 pumps oxygen into the buffer space 12 from a vicinity of the outer pump electrode 23, but this configuration is non-limiting. For example, oxygen may be pumped into the buffer space 12 from a vicinity of the reference electrode 42. With this configuration, the following is possible. In comparison with, for example, a case in which oxygen is pumped to the inside from an external measurement-object gas, oxygen can be pumped into the buffer space 12 at a low applied voltage because the reference gas (in this case, air) has a higher oxygen concentration than the measurement-object gas. In contrast, in the case where oxygen is pumped into the buffer space 12 from the vicinity of the outer pump electrode 23, the voltage Vp0s of the variable power supply 17 needs to be relatively high because, in particular, if a vicinity of the outer pump electrode 23 is a low-oxygen atmosphere, it is necessary to produce oxygen ions by reducing carbon monoxide, water, or the like present in the measurement-object gas.

In the embodiment described above, the second diffusion-rate-limiting portion 13 is present between the buffer space 12 and the first internal space 20, but this configuration is non-limiting. For example, the second diffusion-rate-limiting portion 13 may be omitted, and the buffer space 12 and the first internal space 20 may constitute a single space.

In the embodiment described above, the specific gas concentration detected by the gas sensor 100 is the concentration of NOx, but this configuration is non-limiting, and the specific gas concentration may be the concentration of a different oxide. In the case where the specific gas is an oxide, oxygen is produced when the specific gas itself is reduced in the third internal space 61 as in the embodiment described above, and accordingly, the CPU 92 can detect the specific gas concentration by obtaining a detection value corresponding to the oxygen. Furthermore, the specific gas may be a non-oxide gas, such as ammonia. In the case where the specific gas is a non-oxide gas, the specific gas may be converted into an oxide (e.g., in the case of ammonia, converted into NO). When the converted gas is reduced in the third internal space 61, oxygen is produced, and accordingly, the CPU 92 can detect the specific gas concentration by obtaining a detection value corresponding to the oxygen. For example, in a case where the preliminary pump electrode 16 contains a metal having a catalytic function for promoting oxidation of ammonia, the specific gas can be converted into an oxide in the buffer space 12 via the catalytic function of the preliminary pump electrode 16. A similar configuration is possible for the inner pump electrode 22. Ammonia is converted into an oxide, which is NO, and therefore the measurement of the concentration of ammonia is performed basically by using the same principle as that for the measurement of the concentration of NOx.

In the embodiment described above, the CPU 92 controls the preliminary pump cell 15 in a manner such that a constant preliminary pump current (target value Ip0s*) flows, but this configuration is non-limiting. For example, the CPU 92 may feedback-control the voltage Vp0s in a manner such that the oxygen concentration in the buffer space 12, which is detected based on the voltage between the preliminary pump electrode 16 and the reference electrode 42, reaches a target value. Alternatively, the CPU 92 may control the voltage Vp0s in a manner such that the lower the oxygen concentration of an outside of the sensor element 101, the greater the amount of oxygen to be pumped into the buffer space 12. In this case, the CPU 92 may detect the oxygen concentration of an outside of the sensor element 101 by using the method described above or obtain the oxygen concentration from a device other than the gas sensor 100. Furthermore, the CPU 92 may control the voltage Vp0s to be a constant voltage.

In the embodiment described above, the target value Ip0s* is set based on the amount of oxygen necessary to increase the minimum oxygen concentration of the measurement-object gas, which is the minimum among oxygen concentrations in various operation conditions of an internal combustion engine, to an oxygen concentration higher than the oxygen concentration of a low-oxygen atmosphere (e.g. oxygen concentration greater than 0.1 vol %, greater than or equal to 0.2 vol %, greater than or equal to 1 vol %, or the like). However, this configuration is non-limiting. For example, the target value Ip0s* may be set to a value such that the pump current Ip0 does not decrease to a negative value even in a case where a measurement-object gas having a minimum oxygen concentration, which is the minimum among oxygen concentrations in various operation conditions of an internal combustion engine, is introduced into the measurement-object gas flow section of the sensor element 101. That is, the preliminary pump cell 15 may "prevent the measurement-object gas from reaching the first internal space 20 in a state in which the measurement-object gas is a low-oxygen atmosphere" by ensuring that "the pump current Ip0 does not decrease to a negative value". In any case, the amount of oxygen to be pumped into the buffer space 12 by the preliminary pump cell 15 may be set by experimentation in a manner such that, in accordance with a range of fluctuations a component of the measurement-object gas may experience, a decrease in measurement accuracy is suppressed within the range of fluctuations (e.g., in a manner such that, as illustrated in FIGS. 4 and 5, a state in which the sensitivity of the pump current Ip2 to the concentration of NOx decreases does not easily occur.

Figure 9:
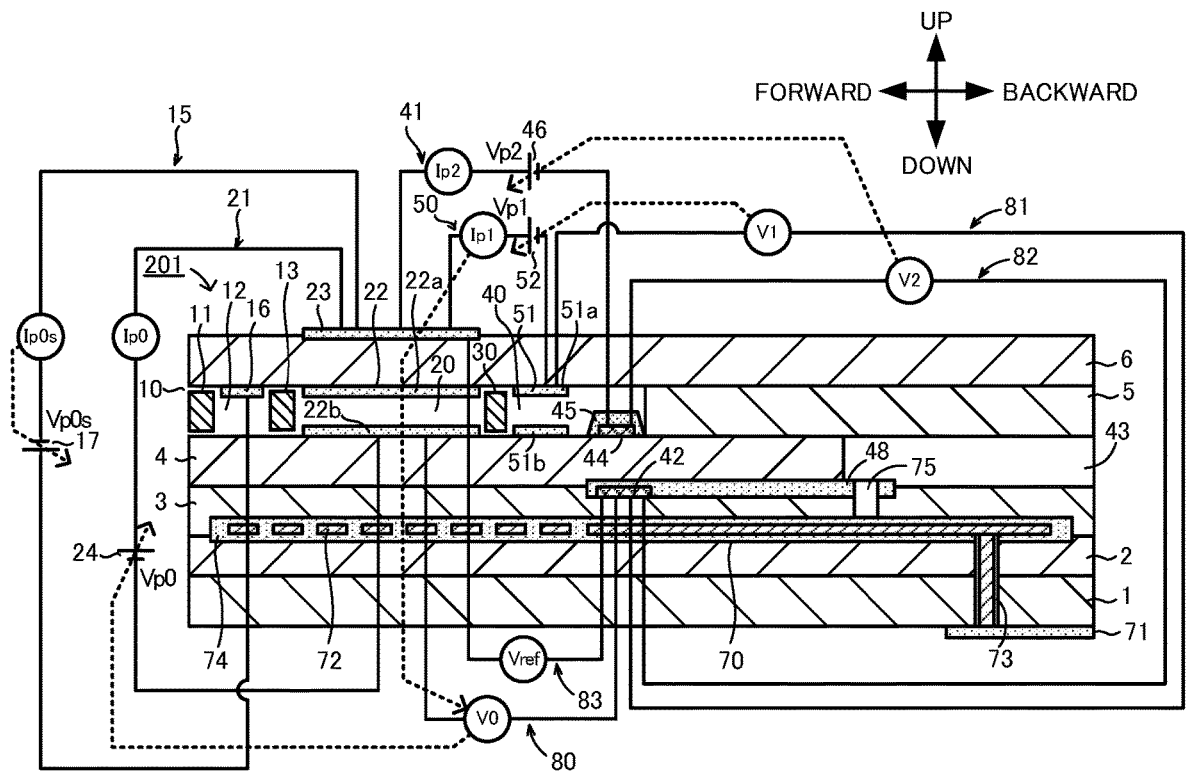
FIG. 9 is a schematic cross-sectional view of a sensor element 201.

In the embodiment described above, the sensor element 101 of the gas sensor 100 includes the first internal space 20, the second internal space 40, and the third internal space 61, but this configuration is non-limiting. For example, the third internal space 61 may not be included as in a sensor element 201, which is illustrated in FIG. 9. In the sensor element 201, which is a modified example illustrated in FIG. 9, the gas inlet port 10, the first diffusion-rate-limiting portion 11, the buffer space 12, the second diffusion-rate-limiting portion 13, the first internal space 20, the third diffusion-rate-limiting portion 30, and the second internal space 40 are formed adjacent to one another in such a manner as to be in communication with one another in this order, between the lower surface of the second solid electrolyte layer 6 and the upper surface of the first solid electrolyte layer 4. Furthermore, the measurement electrode 44 is disposed on the upper surface of the first solid electrolyte layer 4 within the second internal space 40. The measurement electrode 44 is covered with a fourth diffusion-rate-limiting portion 45. The fourth diffusion-rate-limiting portion 45 is a film formed of a ceramic porous member containing, for example, alumina ($Al_2O_3$). As with the fourth diffusion-rate-limiting portion 60 of the embodiment described above, the fourth diffusion-rate-limiting portion 45 serves to limit the amount of NOx flowing into the measurement electrode 44. Furthermore, the fourth diffusion-rate-limiting portion 45 functions as a protective film for the measurement electrode 44. A ceiling electrode portion 51a of the auxiliary pump electrode 51 is formed to extend to a position immediately above the measurement electrode 44. The sensor element 201, configured as described above, can also detect the concentration of NOx based on, for example, the pump current Ip2 as with the embodiment described above. In this case, a vicinity of the measurement electrode 44 functions as a measurement chamber.

In the embodiment described above, the outer pump electrode 23 serves as the following electrodes: the measurement-object gas-side electrode (outer preliminary pump electrode) of the preliminary pump cell 15, an outer main pump electrode of the main pump cell 21, an outer auxiliary pump electrode of the auxiliary pump cell 50, and an outer measurement electrode of the measurement pump cell 41. However, this configuration is non-limiting. One or more of the outer preliminary pump electrode, the outer main pump electrode, the outer auxiliary pump electrode, and the outer measurement electrode may be an additional electrode, other than the outer pump electrode 23. The additional electrode may be provided outside of the element body and be in contact with a measurement-object gas.

In the embodiment described above, the element body of the sensor element 101 is a layered body including a plurality of solid electrolyte layers (layers 1 to 6), but this configuration is non-limiting. It is sufficient that the element body of the sensor element 101 include at least one oxygen-ion-conductive solid electrolyte layer and a measurement-object gas flow section be provided in the interior. For example, referring to FIG. 1, each of the layers 1 to 5, other than the second solid electrolyte layer 6, may be a layer formed of a material other than a solid electrolyte (e.g., a layer formed of alumina). In this case, the electrodes to be included in the sensor element 101 may be disposed on the second solid electrolyte layer 6. For example, the measurement electrode 44 of FIG. 1 may be disposed on the lower surface of the second solid electrolyte layer 6. Furthermore, the reference gas introduction space 43 may be provided in the spacer layer 5 instead of the first solid electrolyte layer 4; the air introduction layer 48 may be provided between the second solid electrolyte layer 6 and the spacer layer 5 instead of being provided between the first solid electrolyte layer 4 and the third substrate layer 3; and the reference electrode 42 may be provided behind the third internal space 61 and on the lower surface of the second solid electrolyte layer 6.

In the embodiment described above, the controller 90 sets (feedback-controls) the target value V0* of the electromotive force V0 based on the pump current Ip1 in a manner such that the pump current Ip1 reaches a target value Ip1*, and the controller 90 feedback-controls the pump voltage Vp0 in a manner such that the electromotive force V0 reaches the target value V0*. However, the controller 90 may perform a different control. For example, the controller 90 may feedback-control the pump voltage Vp0 based on the pump current Ip1 in a manner such that the pump current Ip1 reaches a target value Ip1*. That is, the controller 90 may not obtain the electromotive force V0 from the oxygen partial pressure detection sensor cell 80 for controlling the main pump or set the target value V0*; the controller 90 may directly control the pump voltage Vp0 (therefore, control the pump current Ip0) based on the pump current Ip1.

The "minimum oxygen concentration, which is the minimum among oxygen concentrations in various operation conditions of an internal combustion engine", described above, may be, for example, −11 vol % (value of 11 in terms of air-fuel ratio for gasoline engines). For example, when setting the target value Ip0s* in the manner described in the above embodiment, the following is possible: in a case where a measurement-object gas having an oxygen concentration of −11 vol % flows into the buffer space 12, an amount of oxygen is necessary to increase the oxygen concentration of the measurement-object gas to an oxygen concentration higher than that of a low-oxygen atmosphere (the higher oxygen concentration may be greater than 0.1 vol %, preferably greater than or equal to 0.2 vol %, and more preferably greater than or equal to 1 vol %), and the target value Ip0s* may be set based on the amount of oxygen.

It is preferable that the preliminary pump cell 15 pump oxygen into the buffer space 12 in a manner such that, even in a case where a measurement-object gas having any oxygen concentration that is within a range of −11 vol % or greater and 0.1 vol % or less flows into the buffer space 12, the measurement-object gas reaching the first internal space 20 has an oxygen concentration (=oxygen concentration at the exit of the second diffusion-rate-limiting portion 13) of greater than 0.1 vol %. In Experimental Examples 1 to 8, described above, the oxygen concentration of the measurement-object gas reaching the second internal space 40 (=oxygen concentration at the exit of the third diffusion-rate-limiting portion 30) was examined, and the oxygen concentration was found to be 0.1 vol %. Accordingly, it is believed that, since the oxygen concentration in a vicinity of the auxiliary pump electrode 51 was less than or equal to 0.1 vol %, the auxiliary pump electrode 51 needed to contain Au. On the other hand, as can be seen from the above-described magnitude relationship between the oxygen concentrations in vicinities of the electrodes in the measurement-object gas flow section, the oxygen concentrations in vicinities of the preliminary pump electrode 16 and the inner pump electrode 22 were greater than 0.1 vol %, and accordingly, it is believed that reduction of NO did not occur regarding the preliminary pump electrode 16 or the inner pump electrode 22 although neither of the electrodes contained Au. Hence, when the preliminary pump cell 15 pumps oxygen into the buffer space 12 in a manner such that, even in a case where a measurement-object gas having any oxygen concentration that is within the range of −11 vol % or greater and 0.1 vol % or less flows into the buffer space 12, the measurement-object gas reaching the first internal space 20 has an oxygen concentration greater than 0.1 vol %, the following is possible: even in the case where neither the preliminary pump electrode 16 nor the inner pump electrode 22 contains a noble metal having a catalytic activity suppression ability, it is more reliably unlikely that reduction of a specific gas due to the electrode or reduction of an oxide derived from the specific gas due to the electrode will occur. That is, more reliably, it is possible to eliminate the need for inclusion of a noble metal having a catalytic activity suppression ability in the preliminary pump electrode 16 and the inner pump electrode 22. Furthermore, it is preferable that the CPU 92 control the preliminary pump cell 15 in a manner such that oxygen is pumped to the inside as just described. For example, when setting the target value Ip0s* in the manner described in the above embodiment, the target value Ip0s* may be set to a value such that, even in a case where a measurement-object gas having an oxygen concentration of −11 vol % flows into the buffer space 12, the oxygen concentration of the measurement-object gas reaching the first internal space 20 can be increased to a value higher than 0.1 vol %. Similarly, in the case where "the CPU 92 controls the voltage Vp0s to be a constant voltage", as described in the above modified example, the target value (constant value) of the voltage Vp0s may be set in a manner such that, with a pump current Ip0s that flows in a state in which the voltage Vp0s is controlled at a constant value, the oxygen concentration of −11 vol % of a measurement-object gas that flows into the buffer space 12 can be increased to an oxygen concentration greater than 0.1 vol %. In the case where "the CPU 92 feedback-controls the voltage Vp0s in a manner such that the oxygen concentration in the buffer space 12 reaches a target value", as described in the above modified example, the target value of the oxygen concentration in the buffer space 12 (target value of the voltage between the preliminary pump electrode 16 and the reference electrode 42) may be set to a value slightly above 0.1 vol % (or a value greater than 0.1 vol % with a predetermined margin). In the case where "the CPU 92 controls the voltage Vp0s in a manner such that the lower the oxygen concentration of an outside of the sensor element 101, the greater the amount of oxygen to be pumped into the buffer space 12", as described in the above modified example, the following is possible: the correspondence relationship between the oxygen concentration of an outside of the sensor element 101 and the target value of the voltage Vp0s may be set in advance in a manner such that, even in a case where a measurement-object gas having any oxygen concentration that is within the range of −11 vol % or greater and 0.1 vol % or less flows into the buffer space 12, the oxygen concentration of the measurement-object gas reaching the first internal space 20 can be increased to a value higher than 0.1 vol %, and accordingly, the CPU 92 may control the voltage Vp0s based on the correspondence relationship. Furthermore, it is preferable that the preliminary pump cell 15 pump oxygen into the buffer space 12 in a manner such that the measurement-object gas reaching the first internal space 20 has an oxygen concentration greater than or equal to 1 vol %. More specifically, it is preferable that oxygen be pumped into the buffer space 12 in a manner such that, even in a case where a measurement-object gas having any oxygen concentration that is within the range of −11 vol % or greater and less than 1 vol % flows into the buffer space 12, the measurement-object gas reaching the first internal space 20 has an oxygen concentration greater than or equal to 1 vol %. With this configuration, it is possible, even more reliably, to eliminate the need for inclusion of a noble metal having a catalytic activity suppression ability in the preliminary pump electrode 16 and the inner pump electrode 22. Furthermore, it is preferable that the CPU 92 control the preliminary pump cell 15 in a manner such that oxygen is pumped to the inside as just described.

In the embodiment described above, the main pump cell 21 may pump oxygen from the first internal space 20 in a manner such that the oxygen concentration of the measurement-object gas reaching the second internal space 40 does not become less than 0.1 vol %. With this configuration, the oxygen concentration in a vicinity of the inner pump electrode 22 is suppressed from decreasing. Hence, in the case where the inner pump electrode 22 contains no noble metal having a catalytic activity suppression ability, it is more reliably unlikely that reduction of a specific gas due to the inner pump electrode 22 or reduction of an oxide derived from the specific gas due to the inner pump electrode 22 will occur. Furthermore, it is preferable that the CPU 92 control the main pump cell 21 in a manner such that oxygen is pumped to the outside as just described. For example, an allowable range of the above-described target value V0* may be set in advance by experimentation. The allowable range may be a range such that the measurement-object gas reaching the second internal space 40 is prevented from having an oxygen concentration less than 0.1 vol %. Further, when setting the target value V0* based on the pump current Ip1, the CPU 92 may set the target value V0* to be within the allowable range.

What is claimed is:

1. A gas sensor comprising:
   an element body including an oxygen-ion-conductive solid electrolyte layer, a measurement-object gas flow section being provided within the element body to allow a measurement-object gas to be introduced into the measurement-object gas flow section and flow through the measurement-object gas flow section;
   a main pump cell that pumps oxygen from a first internal space to adjust an oxygen concentration of the first internal space, the first internal space being provided in the measurement-object gas flow section;
   an auxiliary pump cell that pumps oxygen from a second internal space to adjust an oxygen concentration of the second internal space, the second internal space being provided downstream of the first internal space in the measurement-object gas flow section;
   a preliminary pump cell that pumps oxygen into a preliminary chamber to prevent the measurement-object gas from reaching the first internal space in a state in which the measurement-object gas is a low-oxygen atmosphere, the preliminary chamber being provided upstream of the first internal space in the measurement-object gas flow section;
   a measurement electrode disposed on an inner peripheral surface of a measurement chamber, the measurement chamber being provided downstream of the second internal space in the measurement-object gas flow section;

a reference electrode that is disposed within the element body and to which a reference gas is to be introduced, the reference gas serving as a reference for detecting a specific gas concentration in the measurement-object gas;

a measurement voltage detection sensor cell that detects a measurement voltage present between the reference electrode and the measurement electrode; and a controller configured to obtain, based on the measurement voltage, a detection value according to oxygen produced in the measurement chamber and, based on the detection value, detect the specific gas concentration in the measurement-object gas, the oxygen being oxygen derived from the specific gas, wherein the preliminary pump cell includes an inner preliminary pump electrode disposed in the preliminary chamber, the main pump cell includes an inner main pump electrode disposed in the first internal space, the auxiliary pump cell includes an inner auxiliary pump electrode disposed in the second internal space, the inner preliminary pump electrode, the inner main pump electrode, the inner auxiliary pump electrode, and the measurement electrode each contain a noble metal having catalytic activity, at least one of the inner preliminary pump electrode and the inner main pump electrode contains no noble metal having a catalytic activity suppression ability, the catalytic activity suppression ability being an ability to suppress the catalytic activity of the noble metal having the catalytic activity from being exhibited to the specific gas, and the inner auxiliary pump electrode contains a noble metal having the catalytic activity suppression ability.

2. The gas sensor according to claim 1, further comprising the controller being configured to control the preliminary pump cell in a manner such that a constant preliminary pump current flows through the preliminary pump cell.

3. The gas sensor according to claim 1, further comprising a storage device that stores information related to a relationship formula representing a relationship between the detection value and the specific gas concentration, wherein regardless of whether a measurement-object gas that is outside of the element body is a low-oxygen atmosphere, the controller is configured to detect the specific gas concentration by using the relationship formula stored in the storage device.

4. The gas sensor according to claim 1, wherein the controller is configured to detect the specific gas concentration, the specific gas concentration being a concentration corrected based on an oxygen concentration of the measurement-object gas that is outside of the element body.

5. The gas sensor according to claim 4, further comprising the controller being configured to control the preliminary pump cell in a manner such that a constant preliminary pump current flows through the preliminary pump cell and detect the oxygen concentration of the measurement-object gas that is outside of the element body, the oxygen concentration being detected based on the constant preliminary pump current, a pump current that flows when the main pump cell pumps oxygen from the first internal space in a manner such that the oxygen concentration of the first internal space reaches a target concentration, and the target concentration, wherein the controller is further configured to correct the specific gas concentration by using the detected oxygen concentration.

6. The gas sensor according to claim 1, further comprising a measurement-object gas-side electrode disposed at a portion that is to be exposed to the measurement-object gas that is outside of the element body, wherein the preliminary pump cell pumps oxygen into the preliminary chamber from a vicinity of the measurement-object gas-side electrode.

7. The gas sensor according to claim 1, wherein the measurement-object gas is an exhaust gas from an internal combustion engine, the reference gas is air, and the preliminary pump cell pumps oxygen into the preliminary chamber from a vicinity of the reference electrode.

8. The gas sensor according to claim 1, wherein neither the inner preliminary pump electrode nor the inner main pump electrode contains a noble metal having the catalytic activity suppression ability.

9. The gas sensor according to claim 1, wherein the inner auxiliary pump electrode contains Au as the noble metal having the catalytic activity suppression ability.

10. A sensor element comprising:

an element body including an oxygen-ion-conductive solid electrolyte layer, a measurement-object gas flow section being provided within the element body to allow a measurement-object gas to be introduced into the measurement-object gas flow section and flow through the measurement-object gas flow section;

a main pump cell that pumps oxygen from a first internal space to adjust an oxygen concentration of the first internal space, the first internal space being provided in the measurement-object gas flow section;

an auxiliary pump cell that pumps oxygen from a second internal space to adjust an oxygen concentration of the second internal space, the second internal space being provided downstream of the first internal space in the measurement-object gas flow section;

a preliminary pump cell that pumps oxygen into a preliminary chamber, the preliminary chamber being provided upstream of the first internal space in the measurement-object gas flow section;

a measurement electrode disposed on an inner peripheral surface of a measurement chamber, the measurement chamber being provided downstream of the second internal space in the measurement-object gas flow section; and a reference electrode that is disposed within the element body and to which a reference gas is to be introduced, the reference gas serving as a reference for detecting a specific gas concentration in the measurement-object gas, wherein the preliminary pump cell includes an inner preliminary pump electrode disposed in the preliminary chamber, the main pump cell includes an inner main pump electrode disposed in the first internal space, the auxiliary pump cell includes an inner auxiliary pump electrode disposed in the second internal space, the inner preliminary pump electrode, the inner main pump electrode, the inner auxiliary pump electrode, and the measurement electrode each contain a noble metal having catalytic activity, at least one of the inner preliminary pump electrode and the inner main pump electrode contains no noble metal having a catalytic activity suppression ability, the catalytic activity suppression ability being an ability to suppress the catalytic activity of the noble metal having the catalytic activity from being exhibited to the specific gas, and the inner auxiliary pump electrode contains a noble metal having the catalytic activity suppression ability.

* * * * *